US007108844B2

(12) United States Patent  
Carpentier

(10) Patent No.: US 7,108,844 B2  
(45) Date of Patent: Sep. 19, 2006

(54) USE OF STABILIZED OLIGONUCLEOTIDES FOR PREPARING A MEDICAMENT WITH ANTITUMOR ACTIVITY

(75) Inventor: Antoine F. Carpentier, Paris (FR)

(73) Assignees: Assistance Publique-Hopitaux de Paris, Paris (FR); Institut National de la Sante et de la Recherche Medicale, Paris (FR)

( * ) Notice: Subject to any disclaimer, the term of this patent is extended or adjusted under 35 U.S.C. 154(b) by 401 days.

(21) Appl. No.: 09/967,881

(22) Filed: Sep. 28, 2001

(65) Prior Publication Data

US 2002/0192184 A1   Dec. 19, 2002

Related U.S. Application Data

(63) Continuation-in-part of application No. 09/937,057, filed as application No. PCT/FR00/00676 on Mar. 17, 2000.

(30) Foreign Application Priority Data

Mar. 19, 1999   (FR)   .................................. 99 03433

(51) Int. Cl.  
*A61K 51/00* (2006.01)  
*A61K 48/00* (2006.01)  
*C07H 21/04* (2006.01)

(52) U.S. Cl. ...................... 424/1.11; 514/44; 536/23.1; 536/24.2

(58) Field of Classification Search ................. 514/44; 536/23.1, 24.2, 24.33; 424/1.11  
See application file for complete search history.

(56) References Cited

U.S. PATENT DOCUMENTS

| | | |
|---|---|---|
| 5,663,153 A | 9/1997 | Hutcherson et al. |
| 5,723,335 A | 3/1998 | Hutcherson et al. |
| 5,734,033 A | 3/1998 | Reed |
| 6,001,982 A | 12/1999 | Ravikumar et al. |
| 6,020,475 A | 2/2000 | Capaldi et al. |
| 6,022,691 A | 2/2000 | Bruice et al. |
| 6,069,243 A | 5/2000 | Scozzari |
| 6,121,437 A | 9/2000 | Guzaev et al. |
| 6,153,737 A | 11/2000 | Manoharan et al. |
| 6,160,109 A | 12/2000 | Just et al. |
| 6,160,152 A | 12/2000 | Capaldi et al. |
| 6,166,239 A | 12/2000 | Manoharan |
| 6,169,177 B1 | 1/2001 | Manoharan |
| 6,194,388 B1 | 2/2001 | Krieg et al. |
| 6,207,646 B1 | 3/2001 | Krieg et al. |
| 6,218,371 B1 | 4/2001 | Krieg et al. |
| 6,239,116 B1 | 5/2001 | Krieg et al. |
| 6,429,199 B1* | 8/2002 | Krieg et al. |

FOREIGN PATENT DOCUMENTS

| | | |
|---|---|---|
| EP | 0 468 520 A2 | 7/1990 |
| EP | 0 855 184 A1 | 1/1997 |
| WO | WO 94/25588 | 4/1993 |
| WO | WO 96/02555 | 7/1994 |
| WO | WO 97/44346 | 5/1996 |
| WO | WO 98/18810 | 10/1996 |
| WO | WO 98/55495 | 6/1997 |
| WO | WO 99/12027 | 8/1997 |
| WO | WO 99/26634 | 11/1997 |
| WO | WO 99/51259 | 4/1998 |
| WO | WO 00/62923 | 6/1998 |
| WO | WO 00/16804 | 9/1998 |
| WO | WO 00/21556 | 10/1998 |

OTHER PUBLICATIONS

Donnelly J. Nature Medicine, 11(9): 1354-1356, Nov. 2003.*  
DeGruijl T. D. et al. Nature Medicine, 5(10): 1124-1125, Oct. 1999.*  
Jain R. K. Scientific American, 271(1):58-65, Jul. 1994.*  
Vile et al. Gene Therapy, (7):2-8, 2000.*  
Rochiltz C. F. Swiss Medicine Weekly, 131:4-9, 2001.*  
Verma et al. Nature, vol. 389(6648):239-242, 1997.*  
Britton R. J. Current Opinion in Molecular Therapeutics, 6(1):17-25, 2004.*  
Weiner G. J. Journal of Leukocyte Biology, 68:455-463, 2000.*  
Lonsdorf et al. The Journal of Immunology, 171:3941-3946, 2003.*  
Quan et al. Disease-a-Month, 43(11);745-808, 1997.*  
Tachibana et al. Tokai Journal of Experimental Clinical Medicine, 8(5-6):455-463, 1983.*  
Ballas, Zuhair K. et al., "Induction of NK Activity in Murine and Human Cells by CpG Motifs in Oligodeoxynucleotides and Bacterial DNA," J. of Immunol. 1996, 157: 1840-1845.  
Ishizaka, Y. et al., "Human *ret* proto-oncogene mapped to chromosome 10q11.2," Nat'l Cancer Res. Instit. Aug. 17, 1989 (Short Report).  
LaPlanche, Laurine A. et al., "Phosphorothioate-modified oligodeoxyribonucleotides, III, NMR and UV spectroscopic studies of the $R_p$-$R_p$, $S_p$-$S_p$, and $R_p$-$S_p$ duplexes, $[d(GG_8AATTCC)]_2$, derived from diastereomeric ethyl phosphorothioates," Nucleic Acids Research, vol. 14, No. 22, 1986, pp. 9081-9093.  
Liang, Hua et al., "Activation of Human B Cells by Phosphorothioate Oligodeoxynucleotides," J. Clin. Invest. vol. 98, No. 5, Sep. 1996, pp. 1119-1129.  
Lipford, Grayson B. et al., "CpG-containing synthetic oligonucleotides promote B and cytotoxic T cell responses to protein antigen: a new class of vaccine adjuvants," Eur J. Immunol. 1997, 27:2340-2344.

(Continued)

*Primary Examiner*—Sheela Huff  
*Assistant Examiner*—David J. Blanchard  
(74) *Attorney, Agent, or Firm*—Oblon, Spivak, McClelland, Maier & Neustadt, P.C.

(57) ABSTRACT

The invention concerns the use of stabilized oligonucleotides comprising at least an octamer motif of the type: 5'-purine-purine-CG-pyrimidine-pyrimidine-$X_1X_2$-3' wherein the pair $X_1$-$X_2$- is AT, AA, CT or TT, for preparing a medicine with antitumor activity.

9 Claims, 14 Drawing Sheets

OTHER PUBLICATIONS

Pirotton, Sabine et al., "Adenine Nucleotides Modulate Phosphatidylcholine Metabolism in Aortic Endothelial Cells," J. or Cellular Physiol. 142:449-457 (1990).

Rodgers, Kathy E. et al., "Investigations into the Mechanism of Immunosuppression Caused by Acute Treatment with *O,O,S*-Trimethyl Phosphorothioate: Generation of Suppressive Macrophages from Treated Animals," Toxicol. And Applied Pharmacol. 88, 270-281 (1987).

Ross, Peter et al., "The Cyclic Diguanylic Acid Regulatory System of Cellulose Synthesis in *Acetobacter xylinum*," J. of Biol. Chem. vol. 265, Issue of Nov. 5 pp. 18933-18943, 1990.

Connell Y.S. et al., "Anti-tumor activity of a CpG-containing oligodeoxynucleotide (ODN) in athymic mice,"Proceedings of the American Association for Cancer Research Annual Meeting, Mar. 1999, vol. 40, p. 299.

US 6,008,200, 12/1999, Krieg (withdrawn)

* cited by examiner

SEQUENCE LISTING

```
<160> NUMBER OF SEQ ID NOS: 48

<210> SEQ ID NO 1
<211> LENGTH: 22
<212> TYPE: DNA
<213> ORGANISM: Artificial sequence
<220> FEATURE:
<223> OTHER INFORMATION: Oligodeoxynucleotide

<400> SEQUENCE: 1
tgactgtgaa ggttagagat ga                                              22

<210> SEQ ID NO 2
<211> LENGTH: 22
<212> TYPE: DNA
<213> ORGANISM: Artificial sequence
<220> FEATURE:
<223> OTHER INFORMATION: Oligodeoxynucleotide

<400> SEQUENCE: 2
tgactgtgaa cgttcgagat ga                                              22

<210> SEQ ID NO 3
<211> LENGTH: 22
<212> TYPE: DNA
<213> ORGANISM: Artificial sequence
<220> FEATURE:
<223> OTHER INFORMATION: Oligodeoxynucleotide

<400> SEQUENCE: 3
tgactgtgaa cgttccagat ga                                              22

<210> SEQ ID NO 4
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 4
tgccagtaac gttacgtgac                                                 20

<210> SEQ ID NO 5
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 5
tgccagtaac gttaggtgac                                                 20
```

-continued

<210> SEQ ID NO 6
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 6
tgccagtaac gttgtgtgac                                                    20

<210> SEQ ID NO 7
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 7
tgccagtaac gttccgtgac                                                    20

<210> SEQ ID NO 8
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 8
tgccagtgac gtcatgtgac                                                    20

<210> SEQ ID NO 9
<211> LENGTH: 22
<212> TYPE: DNA
<213> ORGANISM: Artificial sequence
<220> FEATURE:
<223> OTHER INFORMATION: Oligodeoxynucleotide

<400> SEQUENCE: 9
tgactgtgaa cgttatagat ga                                                 22

<210> SEQ ID NO 10
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 10
tgccagtaac gttatgtgac                                                    20

<210> SEQ ID NO 11
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 11
tgccagtaac gttaagtgac                                                    20

<210> SEQ ID NO 12
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 12
tgccagtaac gttctgtgac                                                    20

<210> SEQ ID NO 13
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 13
tgccagtaac gttttgtgac                                                    20

<210> SEQ ID NO 14
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 14
gtatgacgac gtcatctagc                                                    20

<210> SEQ ID NO 15
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 15
tactgcagac gtcattatgc                                                    20

<210> SEQ ID NO 16
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 16
ataacgttat gtaacgttat                                                    20

<210> SEQ ID NO 17
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 17
atgacgtcat gtgacgtcat                                                    20

<210> SEQ ID NO 18
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 18
atgacgtcat gtaacgttat                                                    20

<210> SEQ ID NO 19

```
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 19
tgaacgttat tgaacgttat                                           20

<210> SEQ ID NO 20
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 20
tggacgtcat tggacgtcat                                           20

<210> SEQ ID NO 21
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 21
tggacgtcat tgaacgttat                                           20

<210> SEQ ID NO 22
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 22
aggacgtcaa tgaacgttaa                                           20

<210> SEQ ID NO 23
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 23
agaacgttaa tgaacgttaa                                           20

<210> SEQ ID NO 24
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 24
aggacgtcaa tggacgtcaa                                           20

<210> SEQ ID NO 25
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 25
```
aggacgtctt gtaacgtttt                                               20

<210> SEQ ID NO 26
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 26
agaacgtttt gtaacgtttt                                               20

<210> SEQ ID NO 27
<211> LENGTH: 19
<212> TYPE: DNA
<213> ORGANISM: Artificial sequence
<220> FEATURE:
<223> OTHER INFORMATION: Oligodeoxynucleotide

<400> SEQUENCE: 27
aggacgtctt gtgacgttt                                                19

<210> SEQ ID NO 28
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 28
ttgacgtcct ttaacgttct                                               20

<210> SEQ ID NO 29
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 29
ttaacgttct ttaacgttct                                               20

<210> SEQ ID NO 30
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 30
ttgacgtcct ttgacgtcct                                               20

<210> SEQ ID NO 31
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 31
taaacgttat aacgttataa cgttat                                        26

<210> SEQ ID NO 32
<211> LENGTH: 26
<212> TYPE: DNA

```
<213> ORGANISM: Artificial sequence
<220> FEATURE:
<223> OTHER INFORMATION: Oligodeoxynucleotide

<400> SEQUENCE: 32
tagacgtcat gacgtcatga cgtcat                                    26

<210> SEQ ID NO 33
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 33
taaacgttat aacgttatga cgtcat                                    26

<210> SEQ ID NO 34
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 34
taaacgttat gacgtcatga cgtcat                                    26

<210> SEQ ID NO 35
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 35
tagacgtcat aacgttataa cgttat                                    26

<210> SEQ ID NO 36
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 36
taaacgttaa aacgttaaaa cgttaa                                    26

<210> SEQ ID NO 37
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 37
tagacgtcaa gacgtcaaga cgtcaa                                    26

<210> SEQ ID NO 38
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 38
taaacgttaa aacgttaaga cgtcaa                                    26
```

<210> SEQ ID NO 39
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 39
taaacgttaa gacgtcaaga cgtcaa                                    26

<210> SEQ ID NO 40
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 40
tagacgtcaa aacgttaaaa cgttaa                                    26

<210> SEQ ID NO 41
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 41
taaacgttct aacgttctaa cgttct                                    26

<210> SEQ ID NO 42
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 42
tagacgtcct gacgtcctga cgtcct                                    26

<210> SEQ ID NO 43
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 43
taaacgttct aacgttctga cgtcct                                    26

<210> SEQ ID NO 44
<211> LENGTH: 28
<212> TYPE: DNA
<213> ORGANISM: Artificial sequence
<220> FEATURE:
<223> OTHER INFORMATION: Oligodeoxynucleotide

<400> SEQUENCE: 44
taaacgtttt aaacgttttta aacgtttt                                 28

<210> SEQ ID NO 45
<211> LENGTH: 28
<212> TYPE: DNA
<213> ORGANISM: Artificial sequence
<220> FEATURE:

```
<223> OTHER INFORMATION: Oligodeoxynucleotide

<400> SEQUENCE: 45
tagacgtctt agacgtctta gacgtctt                                              28

<210> SEQ ID NO 46
<211> LENGTH: 28
<212> TYPE: DNA
<213> ORGANISM: Artificial sequence
<220> FEATURE:
<223> OTHER INFORMATION: Oligodeoxynucleotide

<400> SEQUENCE: 46
taaacgtttt aaacgtttta gacgtctt                                              28

<210> SEQ ID NO 47
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 47
tcaacgttat aacgttataa cgttat                                                26

<210> SEQ ID NO 48
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 48
tcgacgtcat gacgtcatga cgtcat                                                26
```

USE OF STABILIZED OLIGONUCLEOTIDES FOR PREPARING A MEDICAMENT WITH ANTITUMOR ACTIVITY

BACKGROUND OF THE INVENTION

This application is a continuation-in-part of the national phase filing of U.S. Application Ser. No. 09/937,057 filed on Feb. 26, 2002 which claims priority from PCT/FR00/00676 filed on Mar. 17, 2000. Priority to each of these prior applications is expressly claimed, and the entire disclosure and claims of each of these prior applications is hereby incorporated by reference in its entirety. Priority is also claimed to FR 99/03433, filed Mar. 19, 1999.

This invention is in the field of immunostimulatory molecules that are administered to a patient to help the body's immune system respond to a disease, principally a solid, malignant tumor. Specifically, the present invention relates to compositions and methods of use of stabilized oligonucleotides with antitumor activity.

The effective treatment of cancers remains one of the major challenges of medicine today. The effectiveness of conventional surgical therapies or therapies aimed at cytolysis (chemotherapy and radiotherapy) remains very limited in many cancers. For astrocytomas for example, the treatment of which is based mainly on surgical exeresis, and local cerebral irradiation, the survival median is only 4 to 6 months after surgical exeresis and 8 to 10 months with the combination of surgery and radiotherapy. Supplementary chemotherapy prolongs survival in patients under the age of 60, but very modestly, usually by only about 3 months. Under this triple treatment, the survival median remains less than two years for histological grade III (anaplastic astrocytoma) and less than 1 year for grade IV (glioblastoma). The mortality for these two groups is near 100% (Daumas-Duport C. et al. (1988), Cancer 62(10) pp 2152–65).

Stimulation of the immune system in the treatment of cancers has been attempted through the administration of bacterial extracts (Jaeckle K. A. et al. (1990), J. Clin. Oncol. 8(8) pp 1408–18) or bacterial DNA, in particular that of Mycobacterium bovis (MY-1) (Tokunaga T. et al. (1984), JNCI72 pp 955–62). MY-1 is, however, ineffective in increasing survival in a model of glioma in mice (Nakaichi M. et al (1995), J. Vet. Med. Sci. 57(3) pp 583–5). IL-2 (Herrlinger U. et al. (1996), J. Neurooncol. 27(3) pp 193–203) and, more recently, IL-12 (Kishima H. et al. (1998), Br. J. Cancer 78(4) pp 446–53; Jean W. C. et al (1998), Neurosurgery 42(4) pp 850–6) have also been studied.

Unfortunately, previous attempts using bacterial DNA have had limited effectiveness or unacceptable toxicity and, to date, only the Mycobacterium bovis BCG has resulted in clinical applications, and then only in the limited indication of bladder cancer (Soloway M. S. et al. (1988), Urol. Clin. North Am. 15 pp 661–9).

Oligonucleotides are polymers formed by the combination of purine or pyrimidine bases and sugars, in particular ribonucleotides or deoxyribonucleotides. In the natural form, the linkages joining the individual nucleotides are phosphoesters which are sensitive to the nucleases of the human body. Thus, oligonucleotides have a very short in vivo half-life (of about one minute) when they are injected into humans, which limits their biological effects. To prolong the half-life oligonucleotides can be modified to be resistant to nucleases. Several types of stabilized oligonucleotide have thus been created, such as, phosphorothioates or methylphosphonates (Crooke R. M. (1991), Anti-Cancer Drug Design 6 pp 609–46). The most commonly used are phosphorothioate oligonucleotides.

In some applications, oligonucleotides are designed to be complementary to a known DNA sequence and are termed "anti-sense" due to the specific identity and sequence of the nucleotides relative to a native gene. Antisense application of oligonucleotide technology are very well known. Some oligodeoxynucleotides, and in particular some synthetic oligodeoxynucleotides, have biological effects per se due to the inherent nature of the sequences themselves, outside their conventional antisense properties. The injection of oligonucleotides as therapeutic compounds has been explored for many years, and the development of specific sequences and techniques continues to be an important area of research.

Some oligodeoxynucleotides, independently of any known antisense sequence, are known to stimulate, in vitro and in vivo, the proliferation of B lymphocytes and the activity of natural killer (NK) cells, and induce the secretion by the cells of cytokines such as $\alpha$-IFN, $\beta$-IFN, $\gamma$-IFN, IL-6, IL-12 or TNF-$\alpha$ (Yamamoto S. et al (1992), J. Immunol. 148(12) pp 4072–6; Yamamoto T. et al. (1994), Microbiol. Immunol. 38(10), pp 831–6; Yi A. K. et al. (1996), J. Immunol. 157(12) pp 5394–402; Ballas Z. K. et al. (1996), J. Immunol. 157(5) pp 1840–5; Cowdery J. S. et al. (1996), J. Immunol. 156(12) pp 4570–5; Stacey K. J. et al. (1996), J. Immunol. 157(5) pp 2116–22). This set of cytokines directs toward a Th1-type immune response (Chu R. S. et al. (1997), J. Exp. Med. 186(10) pp 1623–31).

One specific group of oligonucleotides that have been the subject of extensive research are characterized by the presence of a "CpG" motif. This terminology indicates that the sequence of the oligonucleotide molecule contains the nucleotides cytosine (C) and guanine (G) with a phosphate backbone and exhibits a characteristic structure and function when administered therapeutically to a patient. The immunostimulatory properties of these oligodeoxynucleotides are in large part dependent on nonmethylated CG motifs (nonmethylated CpG dinucleotides) which are under-represented in mammalian DNA (Kuramoto E. et al. (1992), Jpn. J. Cancer Res., 83 pp 1128–31).

While the authors agree on the fact that the nonmethylated CG motif is essential to the immunostimulatory function, the identity of the other nucleotides in the complete oligonucleotide molecule are also crucial and the two nucleotides adjacent to the CG motif also dictate the immunostimulatory activity. Although numerous sequences have been studied, the data published on the function of the adjacent sequences are contradictory. It should be appreciated that small differences in the nucleotide sequence of the oligonucleotide, and any chemical modifications thereof, can yield dramatic differences in the therapeutic utility in vivo. Also, special injection techniques, formulations, and other therapeutic approaches can be used in combination with the specific sequence of the oligonucleotide to yield important differences in overall therapeutic utility.

Specifically, Krieg A. M. et al. ((1996), Antisense Nucleic Acid Drug Dev. 6(2) pp 133–9) describe a hexameric motif of the type 5' pur-pur-C-G-pyrimidine-pyrimidine 3', whereas application EP 468 520 claims a palindromic hexameric motif. International application WO 9855495 shows that not all the hexamers as defined by Krieg et al. 1996 are immunostimulatory, and that octamers, of sequence 5'-purine purine CG pyrimidine pyrimidine CC-3' (pur-pur-CG-pyr-pyr-CC) or of sequence 5'-purine purine CG pyrimidine pyrimidine CG-3' (pur-pur-CG-pyr-pyr-CG) should be defined to provide immunostimulatory activity.

Other immunostimulatory oligodeoxynucleotides, some which are and some which are not defined as oligonucleotides having a nonmethylated CG motif, have been described in application EP 855 184 and certain binding sequences for eukaryotic transcription factors such as NFκB or the AP-1 family.

Also, the use of immunostimulatory properties of oligodeoxynucleotides with nonmethylated CG-type motif has been applied to several medical fields:

(1) in the field of vaccination, in combination with the antigen, as an adjuvant for stimulating specifically a Th1-type immune response (Davis H. L. et al. (1998), *The Journal of Immunology* 160(2) pp 870–6, European Patent Application EP 855 184, PCT Application WO 98/18810, University of Iowa Research Foundation, and PCT Application WO 98/55495);

(2) in the field of allergy, for modulating the immune response (International Applications WO 98/18810 and WO 98/55495); and (3) in the domain of cancer,
either in combination with a tumor antigen, as an adjuvant of an antitumor vaccine (application EP 855 184; Weiner G. J. et al. (1996), *Proc. Natl. Acad. Sci.* 94, pp 10833–7; Wooldridge J. E. et al. (1997) *Blood* 89(8) pp 2994–8),
or alone as antitumor agents (Connell et al. (1999), *Proceedings of the American association for Cancer Research* 40 pp 299; application EP 468 520; Carpentier A. F. et al. (1999), *Cancer Research* 59, pp 5429–5432.

In the latter case, the antitumor activity of only a few sequences, among those described, has been effectively demonstrated:

Weiner G. J. et al. and Wooldridge J. E. et al. (already cited) who use an oligonucleotide comprising a nonmethylated CG motif of sequence SEQ ID NO: 49 5'-TCTCCCAGCGTGCGCCAT-3', show that this oligonucleotide has no antitumor effect when it is used alone;

Carpentier et al., Tokunaga et al. and Connell et al. (mentioned above), who use a phosphorothiate oligonucleotide of the octameric type (SEQ ID NO: 2 5 'TGACTGTGAACGTTCGAGATGA3'), a nonstabilized palindromic hexameric oligonucleotide (SEQ ID NO: 50 5' ACCGATGACGTCGCCGGTGACG-GCACCACGACGACGGCCA CGTGCT 3') and a hexameric phosphorothioate oligonucleotide of the type 5' purine purine CG pyrimidine pyrimidine 3', respectively, show antitumor activity.

Other than the nonmethylated CG motif, the exact nature of the active sequences of these immunostimulatory oligodeoxynucleotides, for producing antitumor activity, is not clearly defined; in particular, the data published on the nature of the sequences adjacent to the nonmethylated CG motif (2 bases in the 5' direction and 2 bases in the 3' direction (hexameric motifs) or 4 bases in the 3' direction (octameric motif)) are contradictory as are the teachings of the significance of the identity of these sequences.

Recent studies reported by Hartmann G. et al. ((2000), *The Journal of Immunology* 164 pp 1617–24) explain the difficulty in defining the sequence of such oligonucleotides. These data indicate that not all immunostimulatory oligodeoxynucleotides are equivalent and effective for all the contemplated field defined above and that the stimulation of different compartments of the immune system to obtain the desired activity: adjuvant, antiallergic or antitumor activity highly depends on the specific nature and composition of the oligonucleotide sequence.

In addition, the immune mechanisms of tumor rejection are poorly understood and the data for stimulation of the compartments of the immune system, in vitro, as defined above do not make it possible to predict in advance the antitumor effectiveness of a given oligonucleotide, and it is therefore important to test their antitumor activity in vivo.

Furthermore, the toxicity of oligodeoxynucleotides containing a CG-type motif has been reported when used systemically (both intravenous IV) and (intraperitoneal IP) and also must be taken into account for therapeutic applications (See EP 855 184). Consequently, the immunostimulatory oligonucleotides comprising a CG motif of the prior art have varying and random antitumor activities and may be toxic. For this reason, a set of effective, non-toxic immunostimulatory sequences for antitumor use has not been defined.

SUMMARY OF THE INVENTION

The present invention is directed towards compositions and methods of using oligonucleotides having specially selected sequences that enhance the immunostimulatory potential of the CpG motif. In a preferred embodiment, the oligonucleotides of the invention are palindromic in the hexameric motif (pur-pur-CG-pyr-pyr) and are stabilized against intracellular degradation. Certain pairs of bases at the 3' end of the motif 5' pur-pur-CG-pyr-pyr 3' participate, in an essential way, in optimum antitumor activity. Specifically, the authors show that, according to the exact nature and identity of their sequence, the immunostimulatory oligodeoxynucleotides of the invention have differential effects on NK activation, the proliferation of B lymphocytes, and the secretion of IL-12, of IL-6 and γ-INF. The immunostimulatory oligonucleotide sequences of the present invention have optimum antitumor activity, are not toxic, and are suitable for antitumor use in humans or animals.

The present invention includes compositions of and methods using stabilized oligonucleotides which comprise at least one octameric motif of the type 5'-purine-purine-CG-pyrimidine-pyrimidine-$N_1N_2$-3', in which the pair $N_1N_2$ is AT, AA, CT or TT, for preparing a medicament with antitumor activity. In a preferred embodiment, the hexameric motif pur-pur-CG-pyr-pyr is palindromic.

For the purpose of the present invention, the term "oligonucleotide" is intended to mean an oligodeoxynucleotide.

According to a preferred embodiment of the invention, the stabilized oligonucleotides comprise at least one octameric motif selected from the group consisting of AACGTT-$X_1X_2$, GGCGTT-$X_1X_2$, GACGTC-$X_1X_2$, AGCGTC-$X_1X_2$ and in which $X_1X_2$ is AT, AA, CT or TT. In another embodiment, the oligonucleotide is comprised of two or three of these motifs and the motif may or may not be repeated two or three times and may or may not have intervening nucleotides located between each motif.

According to an advantageous arrangement of this preferred embodiment of the invention, the stabilized oligonucleotides preferably comprise at least one of the following octameric motifs: SEQ ID NO: 51 AACGTT-$N_1N_2$ and SEQ ID NO: 53 GACGTC-$N_1N_2$.

In another preferred embodiment of the invention, at least one of the bases of the octameric motif described above can be modified, in particular, at least one of the cytosines can be replaced with a 5-bromocytosine.

In another preferred embodiment of the invention, the stabilized oligonucleotide is selected from the group consisting of the sequences SEQ ID NO: 8 to 48.

In accordance with the invention, the oligonucleotides are stabilised by any chemical means which protects against in vivo degradation. In a preferred embodiment, protection from degradation is conferred by a modified backbone, such as a phosphorothioate backbone, a phosphorodithioate backbone, a phosphodiester-phosphorothioate mixed backbone, or a 5' and/or 3' chemical stabilisation (Crooke R. M. 1991). Preferably, the stabilized oligonucleotides of the present invention are phosphorothioate. In another embodiment, the oligonucleotides are stabilised by inclusion in a colloidal suspension, such as liposomes, polymers, solid lipid particles, or polyalkylcyanoacrylate nanoparticles (Muller, 2000, Eur. J. Pharm. Biopharm. 50: 167–77; Lambert et al., 2001, Adv. Drug Deliv. Rev., 47, 99–112; Delie et al., 2001 Int. J. Pharm. 214, 25–30).

In accordance with the invention, the stabilized oligonucleotides can be used in single-stranded or double-stranded form.

Preferably, the stabilized oligonucleotides can be any length longer than 8 bases or 8 base pairs, preferably more than 20 bases or more than 20 base pairs and preferably between 20 and 100 nucleotides.

In accordance with the present invention, the oligonucleotides can comprise several octameric motifs as defined above, which may or may not be adjacent; they can also comprise other biologically active sequences, such as antisense sequences. The octameric sequences can themselves be included in antisense sequences.

A subject of the present invention is also a method for use of the stabilized oligonucleotides for preparing medicaments intended for the treatment of cancers in humans, whatever their nature and their degree of anaplasia, in particular cancers of the central and peripheral nervous systems, especially astrocytomas, glioblastomas, medulloblastomas, neuroblastomas, melanomas and carcinomas.

The stabilized oligonucleotides can advantageously be coupled, via covalent, ionic or weak attachments, to a molecule or a group of molecules which modify its biological activity, or its tumor affinity, such as, among other possibilities, transferrin, folate, or antibodies directed against tenascine, EDF receptor, transferrin receptor, FGF receptor (Cristiano, 1998, Frontiers in Bioscience 3, 1161–1170; Hudson, 2000, Expert. Opin. Investig. Drugs, 9: 1231–42.

The stabilized oligonucleotides are preferably used via the intratumoral route and direct injection, but they can also be administered via any other route, optionally via multiple routes, and in particular via the intravenous, intraperitoneal, topical, transdermal, subcutaneous, intra-arterial, pulmonary, nasopharyngeal or oral routes, in solution, in aqueous or oily suspension, as a powder or in any pharmaceutically acceptable form.

Also, any of the compositions containing the oligonucleotides of the invention can be administered in one or more doses, or in continuous release, in particular by means of osmotic micropumps, or combined with any physical or chemical means to have a therapeutically effective dose at the tumor site or in the draining lymph nodes. Such means include, but are not limited to, inclusion into colloidal suspensions such as liposomes, polymers (poly(-D,L-lactic acid), solid lipid particles, polyalkylcyanoacrylate nanoparticles (Bendas. 2001 BioDrugs; 15:215–24; Nishioka and Yoshino 2001. Adv. Drug. Deliv. Rev. 47:55–64; Garcia-Chaumont et al., 2000 Pharmacol. Ther.; 87:255–77).

In another embodiment the phosphodiester oligonucleotidic sequences can be directly included into a plasmid (Shoda et al., 2001 J. Leukoc. Biol., 70:103–12), or into the genome of a living organism such as a virus (lentivirus, adenovirus, retrovirus) for gene therapy (Robbins and Ghivizzani, 1998; Pharmacol. Ther. 80:35–47; Galanis et al., 201, Crit. Rev. Oncol. Hematol., 38:177–92); these preparations being used to achieve inflammation at the tumor site or in the draining lymph nodes.

Effective doses will be determined as a function of the age, the state of health and the weight of the patient, and of the type of cancer to be treated. Typically, effective doses in humans are such that, in the case of an intratumoral injection, an oligonucleotide dose of 10 to 1000 µg/g of tumor is obtained in at least a part of the tumor.

In accordance with the invention, the use of the oligonucleotides can be combined in an additive or synergistic way with other therapies, in particular surgery, radiotherapy, chemotherapy, immunotherapy and differentiating therapies.

Also in accordance with the invention, said oligonucleotides are combined with cells of the immune system, such as macrophages, lymphocytes or antigen-presenting cells, adjuvants of immunity, cytokines (such as GM-CSF, IL-2, IFN-gamma), antitumor antibodies, tumor extracts, tumor antigens, or irradiated, genetically modified, or normal, tumor cells.

Besides the arrangements above, the invention also comprises other arrangements, which will emerge from the following description, which refers to the examples of implementation of the use, which is the subject of the present invention, and to the appended drawings.

DESCRIPTION OF THE FIGURES

FIG. 8 illustrates the effect of the oligonucleotide sequences on the antitumor effectiveness (SEQ. ID NO. 2, PT1; SEQ ID NO: 8, AN2).

FIG. 9 illustrates the effect of the sequence of the hexameric motif 5'-purine-purine-CG-pyrimidine-pyrimidine-3' and of the adjacent sequences on the antitumor effectiveness of the oligonucleotides (SEQ ID NO: 8, AN2; SEQ ID NO: 10, AN21).

FIG. 10 illustrates the effect of the 2 bases ($N_1N_2$) adjacent to the 3' sequence of the hexameric motif 5'purine-purine-CG-pyrimidine-pyrimidine-3'on the antitumor effectiveness of the oligonucleotides (SEQ ID NO: 3, AN14; SEQ ID NO: 9, AN15).

FIG. 11 illustrate the effect of various sequences $N_1N_2$ on the antitumor effectiveness of the oligonucleotides (SEQ ID NO: 8, AN2; SEQ ID NO: 11, AN22; SEQ ID NO: 4, AN23; SEQ ID NO: 5, AN24; SEQ ID NO: 12, AN25; SEQ ID NO: 6, AN26; SEQ ID NO: 13 AN27; SEQ ID NO: 7, AN28).

Figure 1:
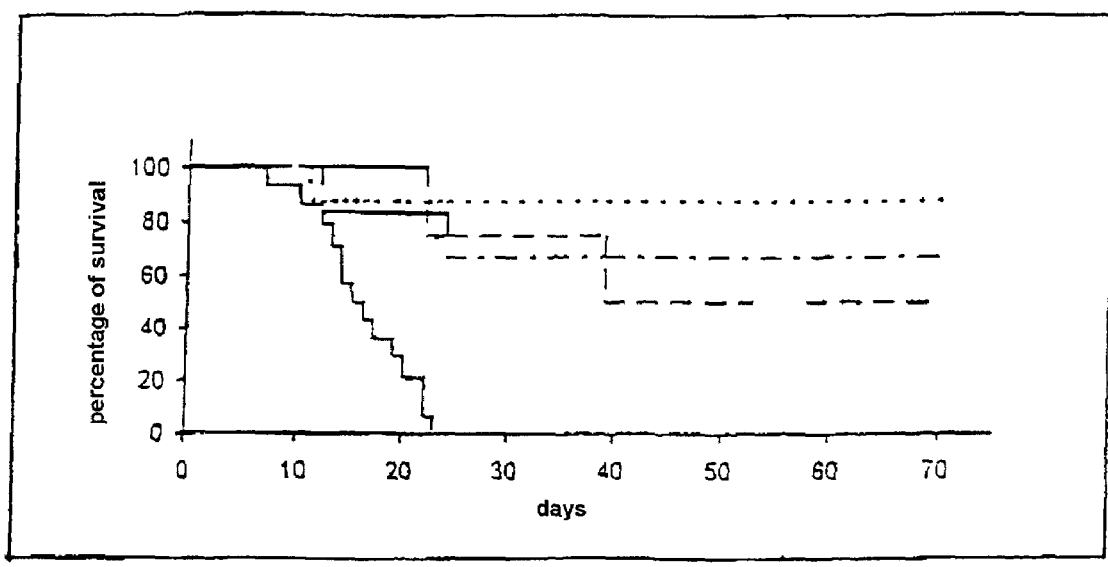
FIG. 1 illustrates the results obtained after an intratumoral injection of the phosphorothioate oligodeoxynucleotide PT1 (SEQ ID NO: 2 5'-TGACTGTGAACGTTCGAGATGA-3'), in the glioma model CNS 1 in the brain of Lewis rats (Kruse C. A. et al. (1994), *J. Neurooncol.* 22 pp 191–200), on the survival time of the control animals (-); PT1 50 µg injected at Day 1 (-.-.-.), PT1 50 µg injected at Day 5 (....) and PT1 50 µg injected at Day 9 (---), after the injection of the tumor cells. The statistical analysis of the results is carried out using the Kaplan-Meier test.

The examples which follow illustrate the invention without, however, limiting it to these particular embodiments.

DETAILED DESCRIPTION OF THE INVENTION

As noted above, the specific nucleotide sequence within the oligonucleotide comprising the CpG motif is particularly significant to the utility of the oligonucleotide as a medicament for antitumor activity. When the immune system is exposed to the olignonucleotide of the invention, cells of the innate immune system, e.g., monocytes, macrophages, antigen presenting cells, and natural killer (NK) cells are activated. Cells of the adaptive system, particularly B cells, are also activated. This immunostimulatory response generated by the CpG oligonucleotides directly activates dendritic cells and macrophages to make cytokines that create a Th-1-like milieu in lymphoid tissues. NK cells are co-stimulated by CpG oligonucleotides and the antigen presenting cell (APC)-derived cytokines, leading to an increase in their innate immune activities, as well as to an IFN-γ dependent feedback loop enhancing APC activation. Also, within about 10–15 minutes of exposure to CpG oligonucleotides, B cells and the elements of the innate immune system, i.e., macrophages and/or dendritic cells, have increased levels of intracellular reactive oxygen species, activation of NFkB, and induction of the mitogen-activated protein kinase (MAPK) pathways. In addition, CpG oligonucleotides can increase the expression of the inducible nitric oxide synthase in macrophages that have been primed with interferon-γ. CpG DNA may also co-stimulate activated T cells.

In the treatment methods of the invention, a solid tumor mass is located within the body of a patient. The tumor mass may be located by a gross inspection, or any standard medical imaging technology such as x-ray, CAT scan, MRI, or other known technique. Once located, the tumor is removed surigcally. In some cases, administration of the immunostimulatory oligonucleotides of the invention will accompany surgical removal of at least a portion of a solid tumor mass. Thus, the administration of the oligonucleotide of the invention may be viewed as a concurrent therapy with other forms of treatment of a solid tumor. For purposes of oligonucleotide administration, a solid tumor is viewed as a non-hematological tumor having a mass which can be removed or stabilized through surgical intervention. To administer or inject the oligonucleotide into the tumor mass, the oligonucleotide may be directly injected with a needle or catheter or virtually any conventional methodology for moving an oligonucleotide molecule across a cell membrane or layer of cells.

Depending on the clinical status of a patient, the oligonucleotide may be directly injected into the tumor, directly injected into the tissue surrounding the tumor, or by intravenous or intraarterial injection. Thus, the administration of the oligonucleotide may be site-specific at the tumor mass, in the tissue surrounding the tumor mass, including the tissue that surrounds a removed tumor mass, or may be remote from the tumor. Furthermore, the administration may be systemic or partially systemic via intravenous, intraarterial, or intraperitoneal administration.

The following examples illustrate the utility of the invention and antitumor activity, while illustrating the effect of certain modifications to the sequence of the CpG motif. Furthermore, extensions of the CpG motif wherein the hexameric palindrome comprising pur-pur-C-G-pyr-pyr is linked at the 3' end to different nucleotide pairs labelled $N_1N_2$ (SEQ ID NO: 51–54). Furthermore, the number of specified motifs present in the oligonucleotide molecule is shown to have a significant effect on the therapeutic utility. Thus, the oligonucleotide of the invention may be comprised of repeating motifs wherein the sequences specified herein are assembled into a molecule having two or three discrete CpG motifs with the sequences, particularly the two nucleotides 5' and the two or four nucleotides 3' of the CG pair as specified herein.

EXAMPLE 1

Effect of an Intratumoral Injection or of an Intraperitoneal Injection of PT1 (SEQ ID NO: 2 5'-TGACTGTGAACGTTCGAGATGA-3') on the Survival of the Animals, in the Glioma Model CNS1 in the Brain of Lewis Rats 1. Procedure:
CNS 1 glioma cells cultured in vitro are grafted into the brain of healthy Lewis rats, in a proportion of $10^5$ cells in the right parietal cortex of the rats (Kruse C. A. et al. (1994), *J. Neurooncol.* 22 pp 191–200).
a) Intratumoral Injection:
50 µg of PT1 in 7 µl of sodium chloride are injected at the tumor site, 1, 5 or 9 days after the graft (group treated on Day 1, n=6; group treated on Day 5, n=8; group treated on Day 9, n=4); a control group (n=14) receives sodium chloride.
b) Intraperitoneal Injection:
50 µg of PT1 are injected intraperitoneally on Day 1 (n =5); a control group receives sodium chloride (n=5).
2. Results:
a) Intratumoral Injection:
They are illustrated in FIG. 1.
The control group shows a mean survival of 15 days and all the animals die before the $23^{rd}$ day The survival of the animals treated with PT1 is greatly increased, with long-term survivals (>90 days) of 67% (p<0.01), of 88% (p<0.002) and of 50% (p<0.02) for the rats treated on Day 1, Day 5 and Day 9, respectively.

All the dead animals exhibit brain tumors at autopsy.

In the surviving rats, none show neurological symptoms and no tumor is found at autopsy carried out on Day 90.

The histological study of the brains reveals no inflammatory, demyelinating or toxic lesion in the parenchyma adjacent to the injection site.

b) Intraperitoneal Injection:
Under these conditions, the PT 1 has no significant effect.

EXAMPLE 2

Comparison of the Effects of an Intratumoral Injection of PT1 (SEQ ID NO: 2 5'-TGACTGT-GAACGTTCGAGATGA-3') on the Survival of the Animals, in the Glioma Model CNS1 of Lewis Rats, with that of an Oligodeoxynucleotide (IMM) Comprising a Nonimmunostimulatory Octanucleotide Sequence (SEQ ID NO: 1 5'-TGACTGT-GAAGGTTAGAGATGA-3')

1. Procedure:
CNS1 glioma cells cultured in vitro are grafted into the brain of healthy Lewis rats, in a proportion of $10^5$ cells in the right parietal cortex of the rats (Kruse C. A. et al. (1994), *J. Neurooncol.* 22 pp 191–200).
On Day 1 after the graft is carried out under the conditions described in Example 1, each rat receives an intratumoral injection of 50 µg of IMM dissolved in 7 µl of sodium chloride, or the vehicle alone (n=5 per group).
2. Results:
The lifespan is not statistically different between the control group, having received the sodium chloride, and the treated group, having received the IMM.

Thus, an oligonucleotide which does not contain any immunostimulatory sequence does not survive, unlike an oligonucleotide which contains such a sequence (Example 1).

EXAMPLE 3

Figure 2:
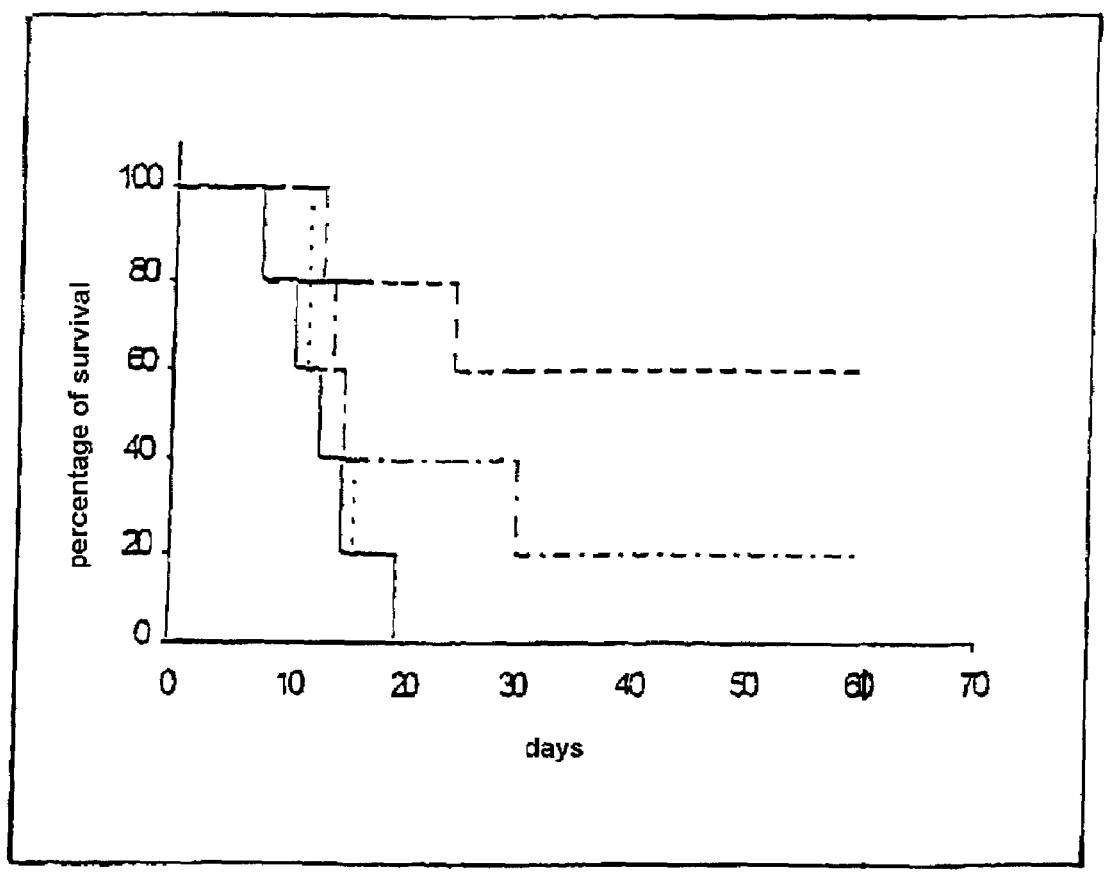
FIG. 2 illustrates the effect of an intratumoral injection on D1 of the phosphorothioate oligodeoxynucleotide PT1 (SEQ ID NO: 2 5'-TGACTGTGAACGTTCGAGATGA-3'), at various doses, in the glioma model CNS1 of Lewis rats, on the survival time of the control animals (-); PT1 50 µg (---), PT1 10 µg (-.-.-.) and PT1 1 µg (....).

Effect of an Intratumoral Injection of PT1 (SEQ ID NO: 2 5'-TGACTGTGAACGTTCGAGATGA-3') at Various Doses on the Survival of the Animals, in the Glioma Model CNS1 of Lewis Rats 1. Procedure:
On Day 1 after the graft is carried out under the conditions described in Example 1, the rats receive an intratumoral injection of 1 µg, 10 µg or 50 µg of PT1 dissolved in 7 µl of sodium chloride, or the vehicle alone (n=5 per group).
2. Results:
Referring to FIG. 2, a survival longer than 90 days is obtained in 60% of the cases (p<0.01) after a single injection of 50 µg, and in 20% of the cases (not significant) after a dose of 10 µg. There is no survivor after a dose of 1 µg (n=5). All the control rats died.

In the surviving rats, none exhibited neurological symptoms and no tumor is found at autopsy carried out on Day 90.

EXAMPLE 4

Investigation of the Mechanism of the Effects of PT1 (SEQ ID NO: 2 5'-TGACTGTGAACGTTCGAGATGA-3'), in vitro and in vivo, on the CNS1 Glioma Cells 1. Procedure:
a) In Vitro
CNS1 glioma cells are placed in culture on Day 0. On Day 1, PT1 at concentrations of 0.05 µM, 0.5 µM and of 5 µM is added to these cells and, on Day 3, the cells are treated with trypsin and their viability is measured.
b) In Vivo: see procedure of Example 1.
2. Results:
a) In Vitro
PT1, at concentrations of 0.05 µM, 0.5 µM and of 5 µM has no direct cytotoxic action on the CNS1 cells after culturing for 48 hours.
b) In Vivo
On the other hand, the immunohistochemical studies show that the injection of 50 µg of PT1 in the tumor triggers a massive infiltration of NK cells, of $CD8^+T$ lymphocytes, of macrophages and of microglial cells, whereas the injection of sodium chloride has no effect. These results suggest that the action of the PT1 is due to activation of the immune system at the tumor site.

EXAMPLE 5

Effect of an Intratumoral Injection of PT1, at a Tumor Site, on the Development of a Tumor Grafted Simultaneously, at a Distance from this Site.

1. Procedure:

The tumor cells are grafted under the conditions described in Example 1, at two separate sites 4 mm apart. On Day 5 after the graft, a group of rats (n=7) receives an intratumoral injection of 50 µg of PT1 dissolved in 7 µl of sodium chloride at just one of these sites, and the control group (n=6) receives the vehicle alone.

2. Results:

All the rats of the control group die within less than 25 days, whereas 44% of the rats of the group treated with PT1 have a prolonged survival (>90 days), (p<0.05).

These results show that the oligonucleotide PT1 has an effect at distance and that the immune response induced at the injection site prevents the development of a tumor grafted simultaneously, at a distance from this site.

EXAMPLE 6

Study of the Immune Memory at 3 Months in the Glioma Model CNS1 of Lewis Rats, after Injection of PT1 (SEQ ID NO: 2 5'-TGACTGTGAACGTTCGAGATGA-3')

1. Procedure:

In rats (n=5) which had been treated with 50 µg of PT1 on Day 5 after the graft, and which had survived due to this treatment with PT1, a new graft of $10^6$ cells is carried out 12 weeks later, in another site of the cerebral cortex, under the conditions described in Example 1. In parallel, a graft of $10^5$ cells is carried out in rats which had not been treated beforehand.

2. Results:

At 90 days, all the animals previously treated with PT1 survived without further treatment. The histological analysis shows that there is no residual tumor, both for the first site of implantation of the tumor cells. All the control animals died and for the second site these results show that the oligonucleotides have a sustained effect which makes it possible to prevent the development of a tumor, even several weeks after the injection of the oligonucleotide. The "memory effect" observed indicates that the oligonucleotide PT1 activates and sets up a specific antitumor immune response.

EXAMPLE 7

Effect of an Intratumoral Injection of PT1 (SEQ ID NO: 2 5'-TGACTGTGAACGTTCGAGATGA-3') or of an Oligodeoxynucleotide (IMM) Comprising a Nonimmunostimulatory Octanucleotide Sequence (SEQ ID NO: 1 5'-TGACTGTGAAGGTTA-GAGATGA-3'), in a Subcutaneous Glial Tumor Model.

1. Procedure:

CNS1 glioma cells cultured in vitro are injected subcutaneously into healthy Lewis rats, in a proportion of $2 \times 10^6$ cells in the right flank (Kruse C. A. et al. (1994), *J. Neurooncol.* 22 pp 191–200). This model makes it possible to monitor more accurately the growth of the tumor, which can be easily evaluated every day in the live animal. In this model, 100% of the animals injected develop a tumor which grows for at least 2 weeks.

Next, on Day 2 after the injection of the tumor cells, 50 µg or 100 µg of PT1, or 50 µg of IMM, in 100 µl of sodium chloride, are injected into the tumor site (group treated with 50 µg of PT1, n=9; group treated with 100 µg of PT1, n=6; group treated with 50 µg of IMM, n=9); a control group (n=9) receives 100 µl of sodium chloride.

The tumor growth is measured every two days and the tumor volume is estimated using the formula: Vol=(length× width×width×π)/6. The animals are sacrificed on Day 12 after the injection of the tumor cells.

Figure 3:
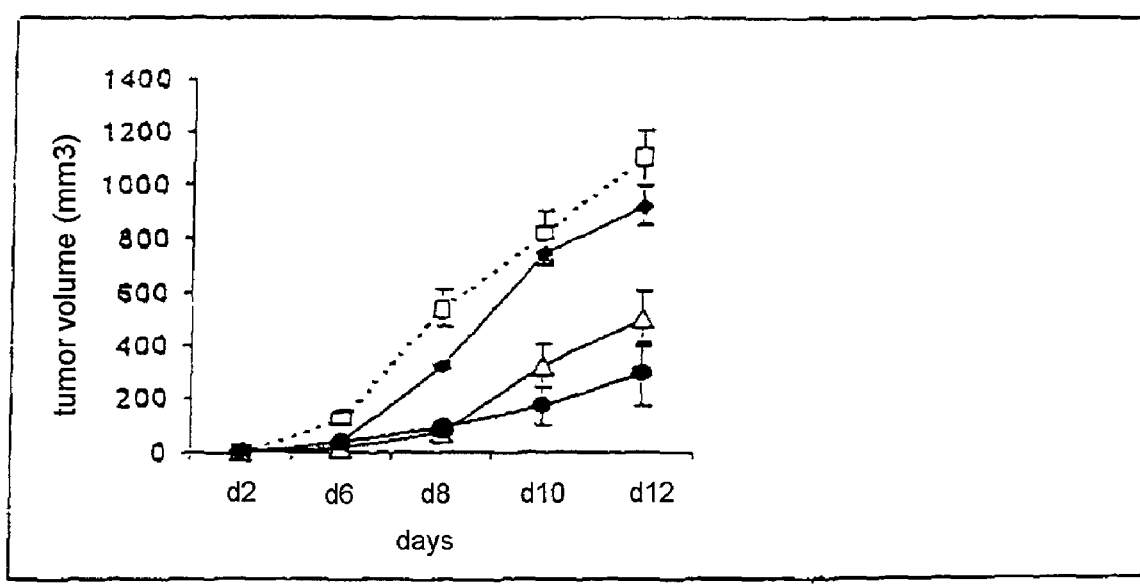
FIG. 3 illustrates the effect of an intratumoral injection of the phosphorothioate oligodeoxynucleotide PT1 (SEQ ID NO: 2 5'- TGACTGTGAACGTTCGAGATGA-3') or of the phosphorothioate oligodeoxynucleotide IMM (SEQ ID NO: 1 5'-TGACTGTGAAGGTTAGAGATGA-3'), in a subcutaneous glial tumor model. On Day 2 after injection of the tumor cells, the animals receive, subcutaneously, at the tumor site, sodium chloride (control -♦-), 50 µg of PT1 (-Δ-), 100 µg of PT1 (-●-) or 50 µg of IMM (-□-). The volume of the tumor is evaluated every two days. The results are expressed as mean ±s.e.m. (Anova Test).

2. Results:

Referring to FIG. 3, in the control group, 9 animals out of 9 developed a tumor, with a mean tumor volume on Day 12 of approximately 900 mm$^3$. In the group treated with IMM, 9 animals out of 9 developed a tumor, with a mean tumor volume on Day 12 of approximately 1 100 mm$^3$. In the group treated with 50 µg PT1, 7 animals out of 9 developed a tumor, with a mean tumor volume on Day 12 of approximately 400 mm$^3$, whereas in the group treated with 100 µg PT1, only 3 animals out of 6 developed a tumor, with a mean tumor volume on Day 12 of approximately 200 mm$^3$. This set of results confirms, therefore, that the PT1 had a marked antitumor effect, linked to the presence of an immunostimulatory sequence and that the effect is dose dependent.

This effect is dose dependent.

EXAMPLE 8

Effect of an Intratumoral Injection of PT1 (Phosphorothioate Oligodeoxynucleotide) or of PE1 (Non-stabilized Oligodeoxynucleotide) in a Subcutaneous Glial Tumor Model; PT1 and PE1 Both Having the Same Immunostimulatory Sequence (SEQ ID NO: 2 5'-TGACTGTGAACGTTC-GAGATGA-3')

1. Procedure:

CNS1 glioma cells cultured in vitro are injected subcutaneously into healthy Lewis rats, in a proportion of $2 \times 10^6$ cells in the right flank, under the conditions described in example 7. Next, on Day 2 after the injection of the tumor cells, 100 µg of PT1 or 100 µg of PE1 are injected into the tumor site (group treated with 100 µg of PT 1 in 100 µl of sodium chloride, n=6; group treated with 100 µg of PE1 in 100 µl of sodium chloride, n=6); a control group (n=6) receives 100 µl of sodium chloride. The tumor growth is measured every two days and the tumor volume is measured as described in Example 7. The animals are sacrificed on Day 12 after the injection of the tumor cells.

Figure 4:
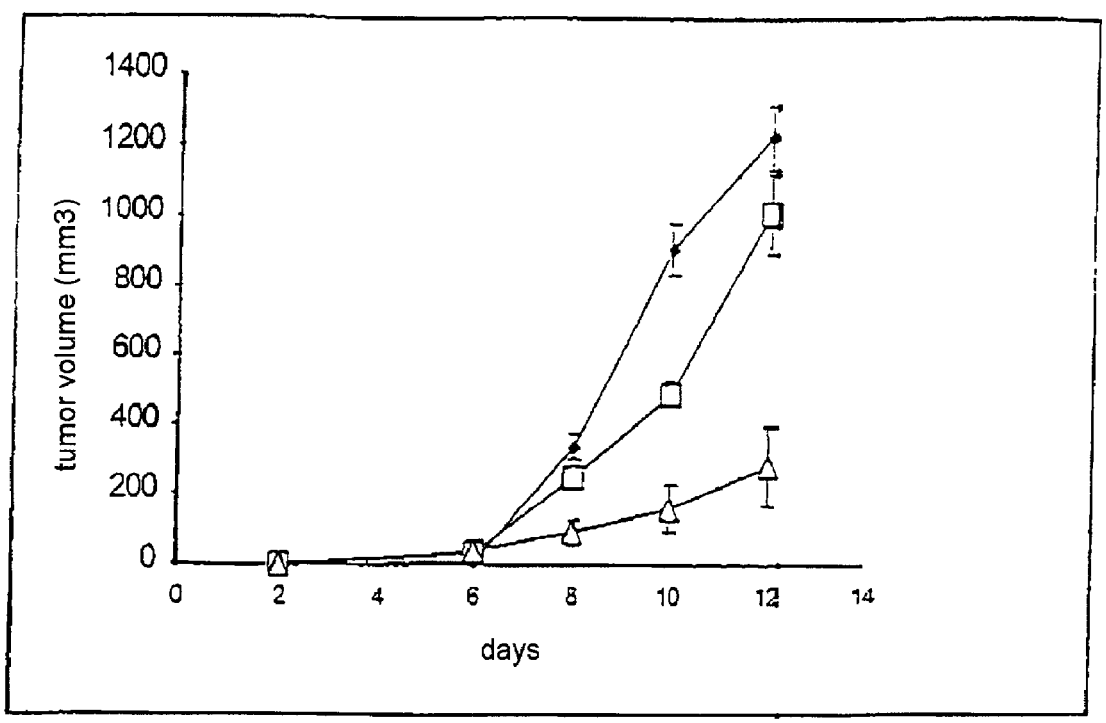
FIG. 4 illustrates the effect of an intratumoral injection of the phosphorothioate oligodeoxynucleotide PT1 or of the phosphodiester oligodeoxynucleotide PE1, both having the SEQ ID NO: 2 (5'-TGACTGTGAACGTTCGAGATGA-3'), in a subcutaneous glial tumor model. On Day 2 after injection of the tumor cells, the animals receive, subcutaneously, at the tumor site, sodium chloride (control -♦-), 100 μg of PE1 (-□-) or 100 μg of PT1 (-Δ-). The volume of the tumor is evaluated every two days. The results are expressed as mean ±s.e.m. (Anova Test).

2. Results:

Referring to FIG. 4, in the control group, 6 animals out of 6 developed a tumor, with a mean tumor volume on Day 12 of approximately 1 200 mm$^3$. In the group treated with PE1, 6 animals out of 6 developed a tumor, with a mean tumor volume on Day 12 of approximately 1 000 mm$^3$. In the group treated with 100 µg PT1, only 3 animals out of 6 developed a tumor, with a mean tumor volume on Day 12 of approximately 200 mm$^3$.

EXAMPLE 9

Effect of an Intratumoral Injection of PT1 (SEQ ID NO: 2 5'-TGACTGTGAACGTTCGAGATGA-3') and of IMM (SEQ ID NO: 1 5'-TGACTGTGAAG-GTTAGAGATGA-3') in the Neuroblastoma Model Neuro2a in A/J Mice 1. Procedure:

The tumor is obtained by injecting one million neuro2a cells into the right flank of A/J mice (Sigal R. K. et al. (1991), *J. Pediatr. Surg.*, 26 pp 389–96). This tumor grows in 15–20 days, generally resulting in the death of the animal or making it necessary to sacrifice it. On Day 2 after the injection of these tumor cells, 50 μg or 100 μg of PT1, or 50 μg of IMM, in 100 μl of sodium chloride, or 100 μl of sodium chloride (control group), are injected into the same site (n=6 animals per group). The tumor growth is measured every four days and the tumor volume is measured as indicated in example 7. The animals are sacrificed on Day 22 after the injection of these tumor cells.

Figure 5:
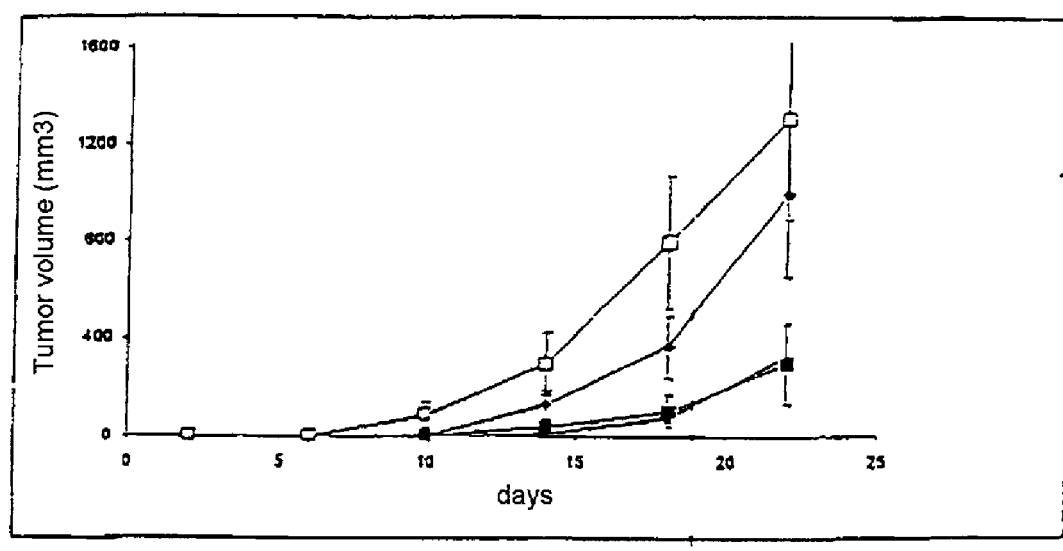
FIG. 5 illustrates the effect of an intratumoral injection of the phosphorothioate oligodeoxynucleotide PT1 (SEQ ID NO: 2 5'-TGACTGTGAACGTTCGAGATGA-3') or of the phosphorothioate oligodeoxynucleotide IMM (SEQ ID NO: 1 5'-TGACTGTGAAGGTTAGAGATGA-3'), in the neuroblastoma model neuro2a in A/J mice (Sigal R. K. et al. (1991), *J. Pediatr. Surg.* 26 pp 389–96). On Day 2 after injection of these tumor cells, the animals receive, subcutaneously, at the tumor site, sodium chloride (control -♦-), 50 μg of PT1 (-■-), 100 μg of PT1 (-π-) or 50 μg of IM(-□-). The volume of the tumor is evaluated every four days. The results are expressed as mean ±s.e.m. (Anova Test).

2. Results:

Referring to FIG. 5, in this model, the mean tumor volume on Day 22 is approximately 800 mm$^3$ in the control group, approximately 1200 mm$^3$ in the group treated with 50 μg of IMM, and approximately 200 mm$^3$ in the groups treated with 50 μg or 100 μg of PT1.

EXAMPLE 10

Effect of a Subcutaneous or Intraperitoneal Injection of PT1 (SEQ ID NO: 2 5'-TGACTGTGAACGTTCGAGATGA-3') at the Dose of 50 μg, in the Neuroblastoma Model Neuro2a in A/J Mice 1. Procedure:

The tumor is obtained according to the procedure described in example 9.

On Day 2 after the injection of the tumor cells, 50 μg of PT1 in 100 μl of sodium chloride, or 100 μl of sodium chloride (control group), are injected either subcutaneously at a distance from the tumor, or intraperitoneally (n=6 animals per group).

The tumor growth is measured every four days and the tumor volume is measured as indicated in example 7. The animals are sacrificed on Day 22 after the injection of the tumor cells.

Figure 6:
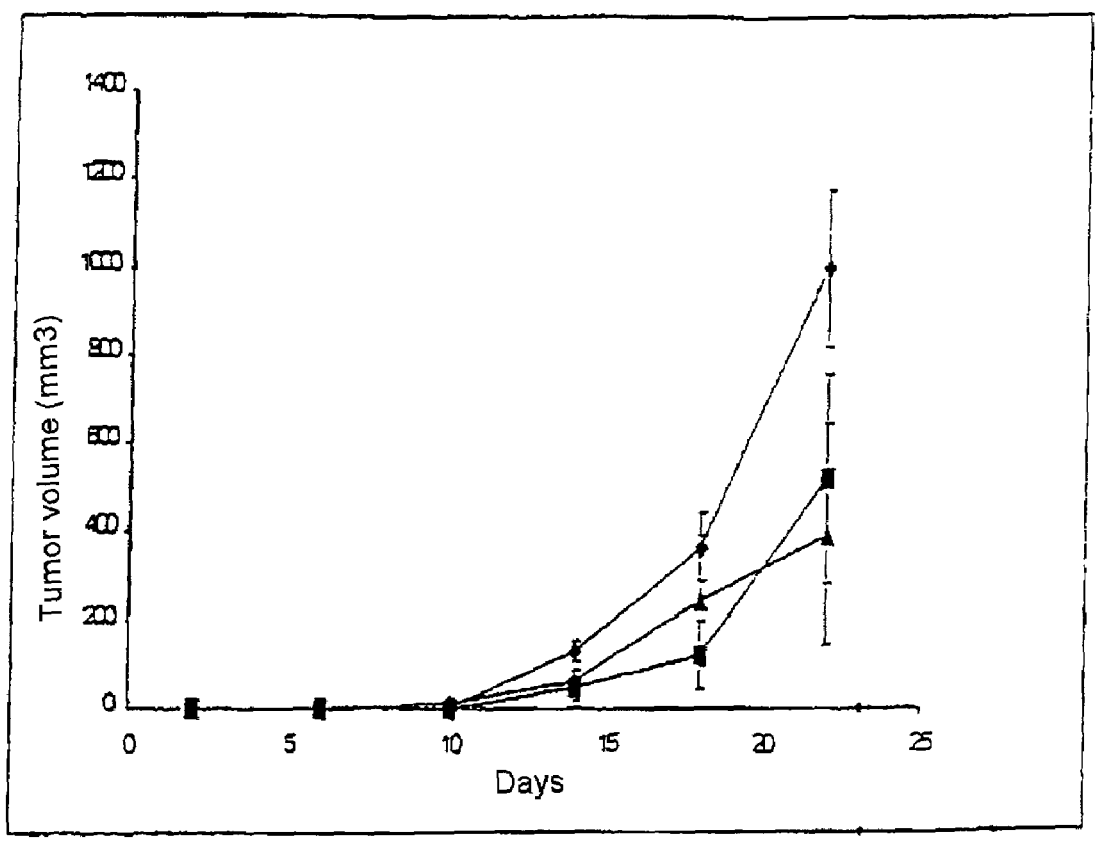
FIG. 6 illustrates the effect of a subcutaneous or intraperitoneal injection of the phosphorothioate oligodeoxynucleotide PT1 (SEQ ID NO: 2 5'-TGACTGTGAACGTTC-GAGATGA-3'), at the dose of 50 μg, in the neuroblastoma model neuro2a in A/J mice (Sigal R. K. et al. (1991), *J. Pediatr. Surg.* 26 pp 389–96). On Day 2 after injection of these tumor cells, the animals (n=6 per group) receive 100 μl of sodium chloride (control group -♦-), or 50 μg of PT1 injected i.p. (-■-) or s.c. at a distance from the tumor (-π-), in 100 μl of sodium chloride.

2. Results:

Referring to FIG. 6, in this model, the mean tumor volume on Day 22 is approximately 1000 mm$^3$ in the control group, approximately 400 mm$^3$ in the group treated with 50 μg of PT1 injected subcutaneously and approximately 500 μm$^3$ in the group treated with 50 μg of PT1 injected intraperitoneally.

EXAMPLE 11

Effect of Repeated Subcutaneous Injection of PT1 (SEQ ID NO: 2 5'-TGACTGTGAACGTTC-GAGATGA-3') or of IMM (SEQ ID NO: 1 5'-TGACTGTGAAGGTTAGAGATGA-3') at the Dose of 10 μg, for 15 Days, in the Neuroblastoma Model Neuro2a in A/J Mice 1. Procedure:

The tumor is obtained according to the procedure described in Example 9.

The tumor growth is measured regularly in all the animals, and when the diameter of the tumor reaches 5 mm, PT1 is injected subcutaneously, around the tumor, for 15 days, at the dose of 10 μg per day in 100 μl of sodium chloride (group treated with PT1, n=7) or IMM is injected subcutaneously, around the tumor, for 15 days, at the dose of 10 μg per day in 100 μl of sodium chloride (group treated with IMM, n=4) or 100 μl of sodium chloride is injected subcutaneously, around the tumor, for 15 days (control group, n=6).

2. Results:

In the control group and in the group treated with the IMM, the tumor growth is not slowed down and all the animals of these two groups die from their tumor. In the group treated with PT1, complete disappearance of the tumor, with no long term recurrence, is observed in 3 mice; in 3 others, the tumors are stabilized for 3 weeks but then recommence their progression until the animals die. These results show that the stabilized immunostimulatory oligonucleotides used according to the invention have a marked intrinsic antitumor effect, linked to the presence of the immunostimulatory sequence and to their stabilization.

EXAMPLE 12

Effect of Stabilizing an Oligonucleotide (SEQ ID NO: 9 5'-TGACTGTGAACGTTATAGATGA-3') on the Antitumor Activity, in a Subcutaneous Glial Tumor Model 1. Procedure:

CNS1 glioma cells cultured in vitro are injected subcutaneously into healthy Lewis rats, in a proportion of 2×10$^6$ cells in the right flank (Kruse C. A. et al. (1994), *J. Neurooncol.* 22 pp 191–200).

On Day 2 after the injection of the tumor cells, 50 μg of the oligonucleotides having the various chemical linkages are injected into the tumor site and the tumor volume is measured on D10 (groups treated with an oligonucleotide of linkage: phosphorothioate (PT, n=9), phosphodiester (PDE, n=8), methylphosphonate (MP, n=9), phosphodiester stabilized in 3' by a dideoxycytosine base (group 3', n=7), or mixed: phosphodiester with the first three linkages in 5' and the last three linkages in 3' of the phosphorothioate type (mixed group, n=9). The control group receives 100 μl of sodium chloride (NaCl n=9).

Figure 7:
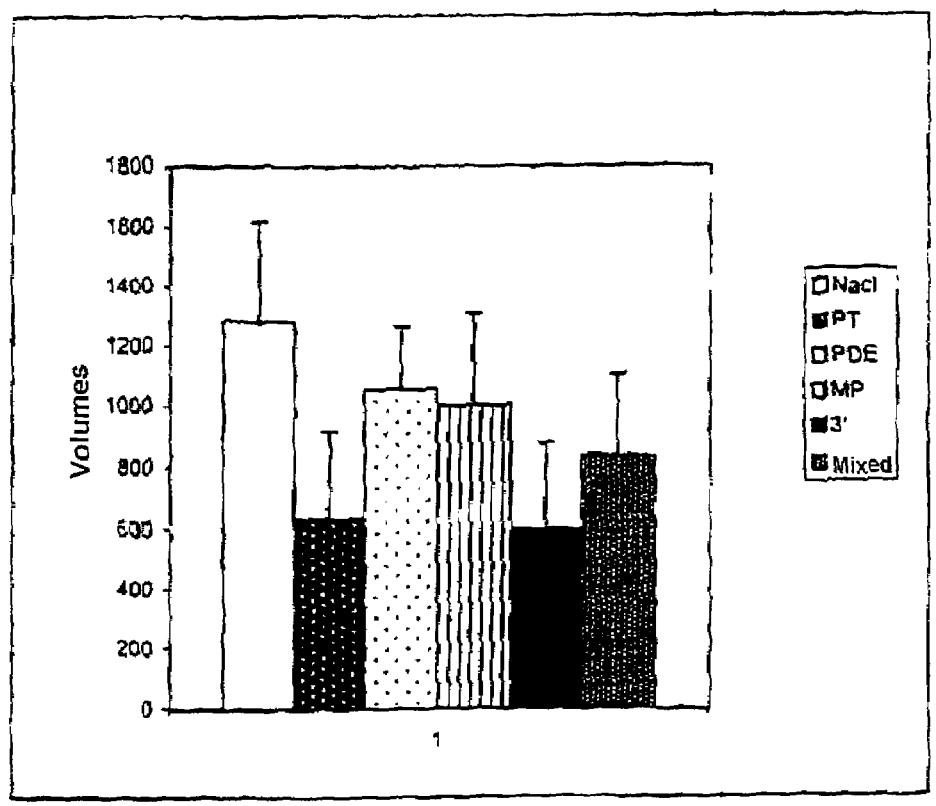
FIG. 7 illustrates the effect of stabilizing an oligonucleotide (SEQ ID NO: 9 5'-TGACTGTGAACGTTATA-GATGA-3') via a linkage of the type phosphorothioate (PT), phosphodiester (PDE), methylphosphonate (MP); phosphodiester stabilized in 3' by a dideoxycytosine base (3') or mixed: phosphodiester with the first 3 linkages in 5' and the last three linkages in 3' of phosphorothioate type (mixed), on the antitumor activity in a subcutaneous glial tumor model. On Day 2 after injection of the tumor cells, the groups of animals receive, subcutaneously, at the tumor site, sodium chloride (NaCl control, n=9) or 50 μg of the oligonucleotides PT (n=9), PDE (n=8), MP (n=9), 3' (n=7) and mixed (n=9). The volume of the tumor is evaluated on D10. The results are expressed as mean ±s.e.m.

2. Results:

Referring to FIG. 7, in this model, the most effective ODNs are the oligonucleotides of type phosphorothioate, stabilized in 3', or mixed, with a decrease in the tumor volume of 50%, 53% and 34%, respectively, with respect to the volume of the controls.

EXAMPLE 13

Figure 10:
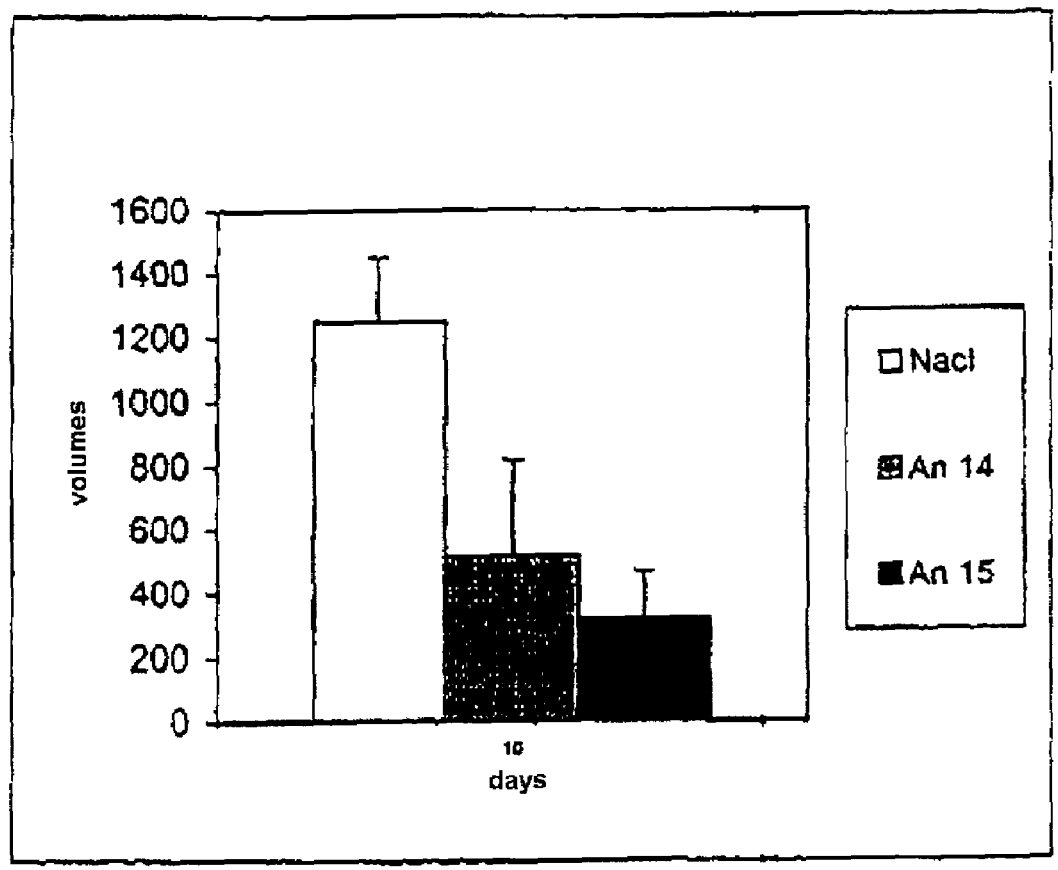
Figure 11:
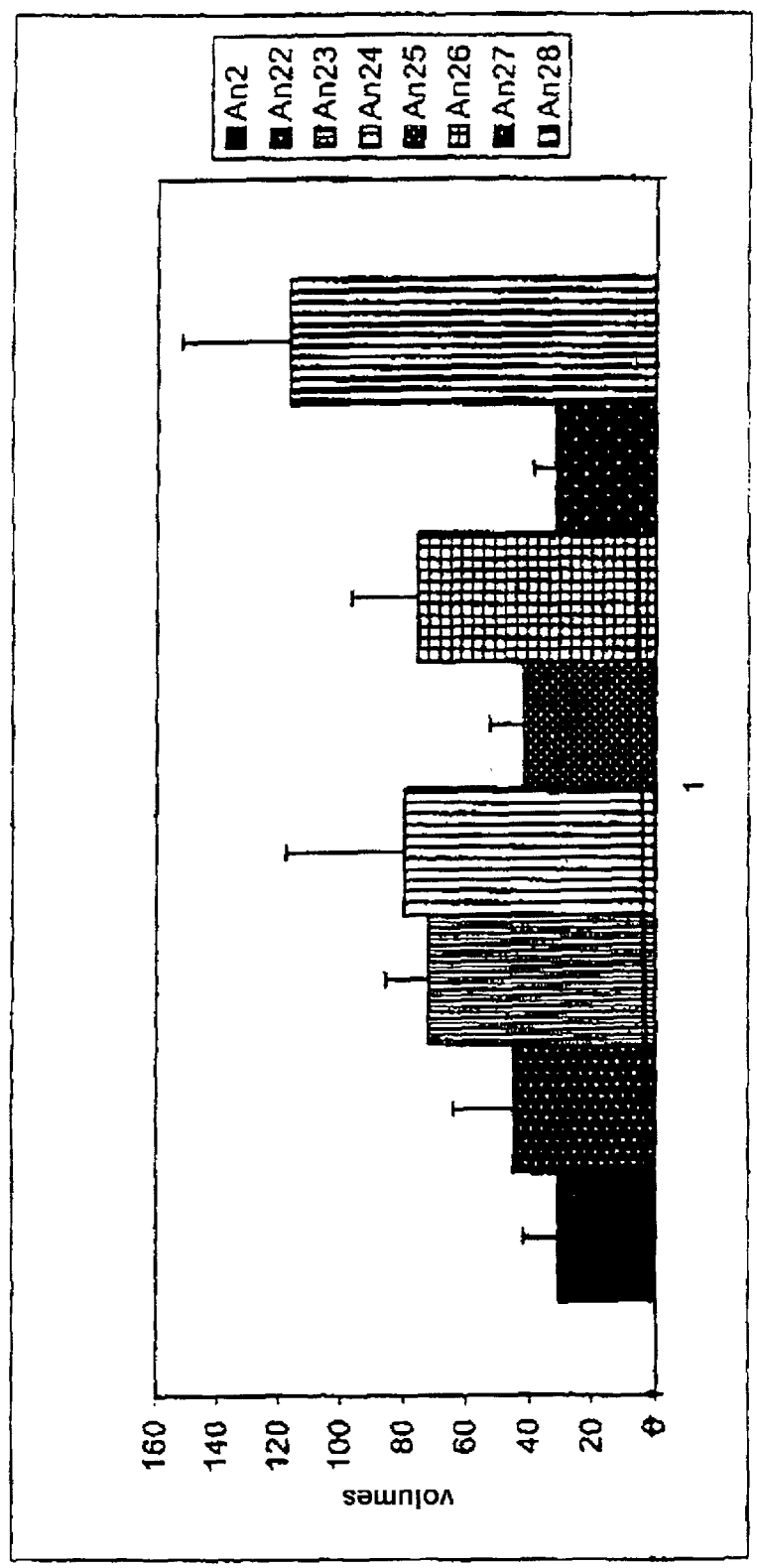

Effect of the Sequences (SEQ ID NO: 51–54) 5'-purine-purine-CG-pyrimidine-pyrimidine-$N_1,N_2$-3' on the Modulation of the Antitumor Activity 1. Procedure:

CNS1 glioma cells cultured in vitro are injected subcutaneously into healthy Lewis rats, in a proportion of 2×10$^6$ cells in the right flank (Kruse C. A. et al. (1994), *J. Neurooncol.* 22 pp 191–200). On Day 2 after the injection of the tumor cells, 50 μg of the various oligonucleotides (SEQ ID NO: 2 to 13) are injected into the tumor site and the tumor volume is measured on Day 10 (FIGS. 8 to 10) or on Day 8 (FIG. 11).

2. Results:

2.1. Effect of the Oligonucleotide Sequence on the Antitumor Effectiveness

Figure 8:
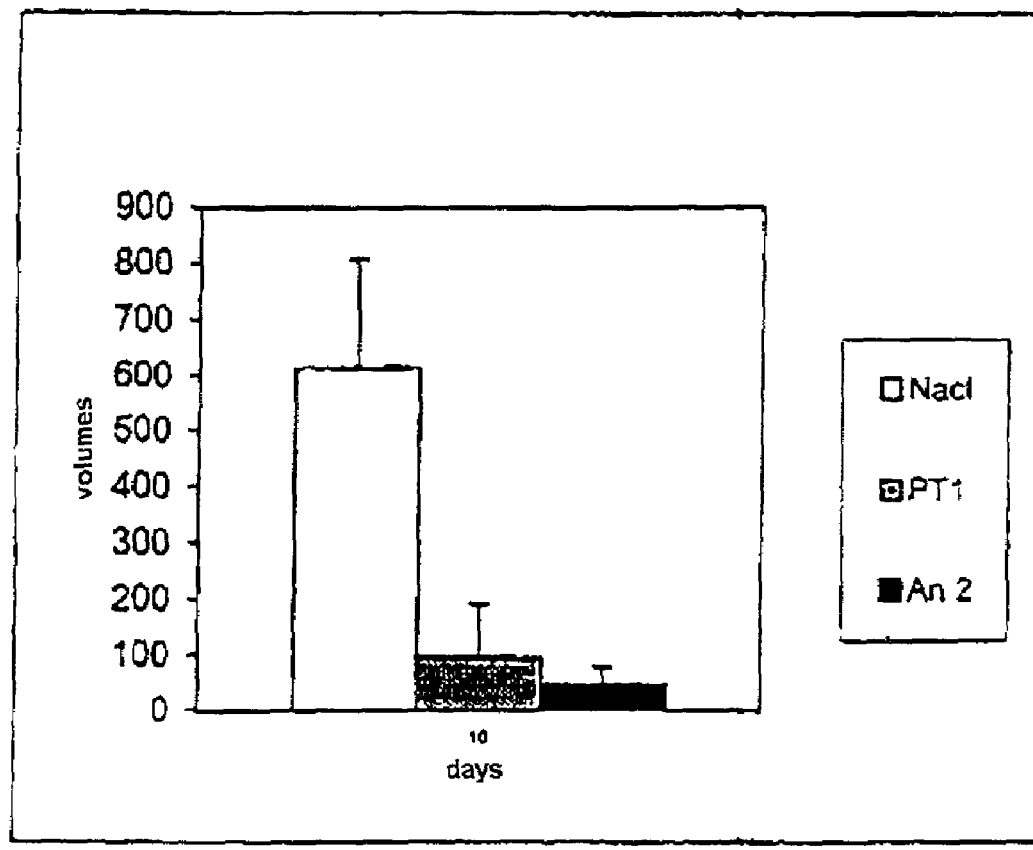
FIGS. 8 to 11 illustrate the effect of the sequences 5'-purine-purine-CG-pyrimidine-pyrimidine-$N_1N_2$-3' on the modulation of the antitumor activity in a subcutaneous glial tumor model. On Day 2 after injection of the tumor cells, the groups of animals (n=6) receive, subcutaneously, at the tumor site, sodium chloride (NaCl control) or 50 μg of the oligonucleotides (SEQ ID NO: 2 to 13). The volume of the tumor is evaluated on Day 8 (FIGS. 8 to 10) or on D10 (FIG. 11). The results are expressed as mean±s.e.m.

Referring to FIG. 8, the oligonucleotide PT1 (SEQ ID NO: 2 5'-TGACTGTGAACGTTCGAGATGA-3') used above (examples 1 to 10) is less effective than the oligonucleotide An 2 (SEQ ID NO: 8 5'-TGCCAGTGACGTCATGTGAC-3'). The difference in effectiveness of these two oligonucleotides is linked either to the sequence of the hexameric motif 5'-purine-purine-CG-pyrimidine-pyrimidine-3' comprising the nonmethylated CG motif (underlined sequence), or to the sequences adjacent to this motif.

2.2. Effect of the Sequence of the Hexameric Motif 5'-Purine-Purine-CG-Pyrimidine-Pyrimidine-3' and of the Adjacent Sequences on the Antitumor Effectiveness of the Oligonucleotides.

Figure 9:
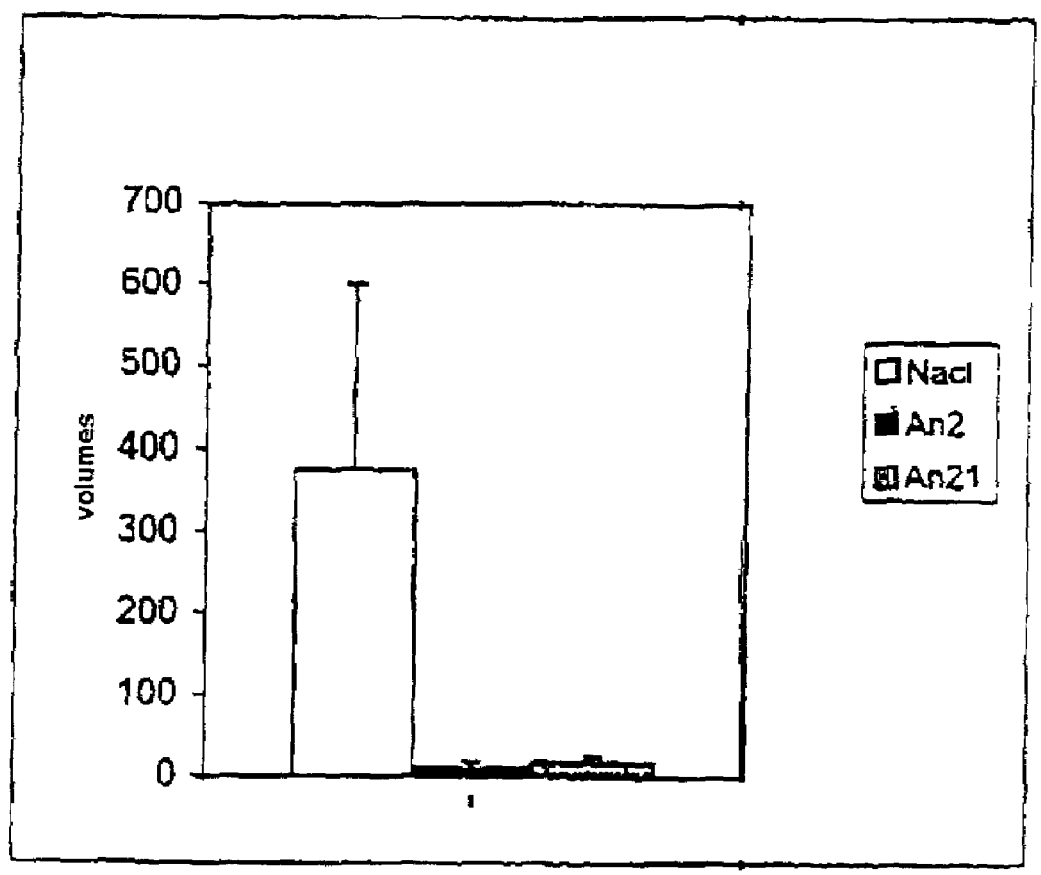

Referring to FIG. 9, oligonucleotides having a different hexameric motif, GACGTC (An2, SEQ ID NO: 8 5'-TGCCAGTGACGTCATGTGAC-3') or AACGTT (An21, SEQ ID NO: 10 5'-TGCCAGTAACGTTATGTGAC-3'), and identical adjacent sequences have the same antitumor effectiveness.

Consequently, the differences in effectiveness observed, in Example 2. 1, between the oligonucleotides PT1 and An2 are linked to the nature of the sequences adjacent to the hexameric motif. The optimum antitumor sequences are found in the adjacent sequences of the oligonucleotide An2.

2.3. Effect of the 2 Bases ($N_1N_2$) Adjacent to the 3' Sequence of the Hexameric motif 5'-purine-purine-CG-pyrimidine-pyrimidine-3' on the Antitumor Effectiveness Referring to FIG. 10, the 2 bases adjacent to the 3' sequence of the hexameric motif modulate the effectiveness of the oligonucleotides, since 2 oligonucleotides which are identical along their entire sequence with the exception of these 2 nucleotides have different effectivenesses, of the order of those previously observed with the oligonucleotides of Example 2.1. Thus, the oligonucleotide An 14 (SEQ ID NO: 3 5'-TGACTGTGAACGTTCCAGATGA-3') is less effective than the oligonucleotide An 15 (SEQ ID NO: 9, 5'-TGACTGTGAACGTTATAGATGA-3'). The nucleotides AT positioned 3' of the hexamenc motif (An2 (FIG. 8) and An 15 (FIG. 10)) make it possible to increase the antitumor effectiveness, whereas the nucleotides CC (An 14, FIG. 10) and CG (PT1, FIG. 8) have less marked antitumor effects.

2.4. Effect of Various Seciuences $X_1X_2$ on the Antitumor Effectiveness

Referring to FIG. 11, the optimum antitumor effect is observed with the sequences $N_1N_2$=AT, AA, CT or TT:

An2 5'-TGCCAGTGACGTCATGTGAC-3'(SEQ ID NO: 8);

An22 5'-TGCCAGTAACGTTAAGTGAC-3'(SEQ ID NO: 11);

An25 5'-TGCCAGTAACGTTCTGTGAC-3'(SEQ ID NO: 12);

An27 5'-TGCCAGTAACGTTTTGTGAC-3'(SEQ ID NO: 13).

The sequences $N_1N_2$=AC, AG, GT and CC and CG (An23 SEQ ID NO: 4 5'-TGCCAGTAACGTTACGTGAC-3'; An24 SEQ ID NO: 5 5'-TGCCAGTAACGTTAGGTGAC-3'; An26 SEQ ID NO: 6 5'-TGCCAGTAACGTTGTGTGAC-3'; An 28 SEQ ID NO: 7 5'-TGCCAGTAACGTTCCGTGAC-3' and PT1 SEQ ID NO: 2 5'-TGACTGTGAACGTTCGAGATGA-3' (see FIG. 8) do not improve the antitumor activity of the oligonucleotides having a hexameric motif 5'-purine-purine-CG-pyrimidine-pyrimidine-3'.

These results show that the set of stabilized oligonucleotides of the type 5'-purine-purine-CG-pyrimidine-pyrimidine-$N_1N_2$-3' with $N_1N_2$=AA, AT, CT or TT have optimized antitumor activity.

EXAMPLE 14

Antitumor Efficacy of an Immunostimulating Oligonucleotide in a Melanoma Model

Figure 12:
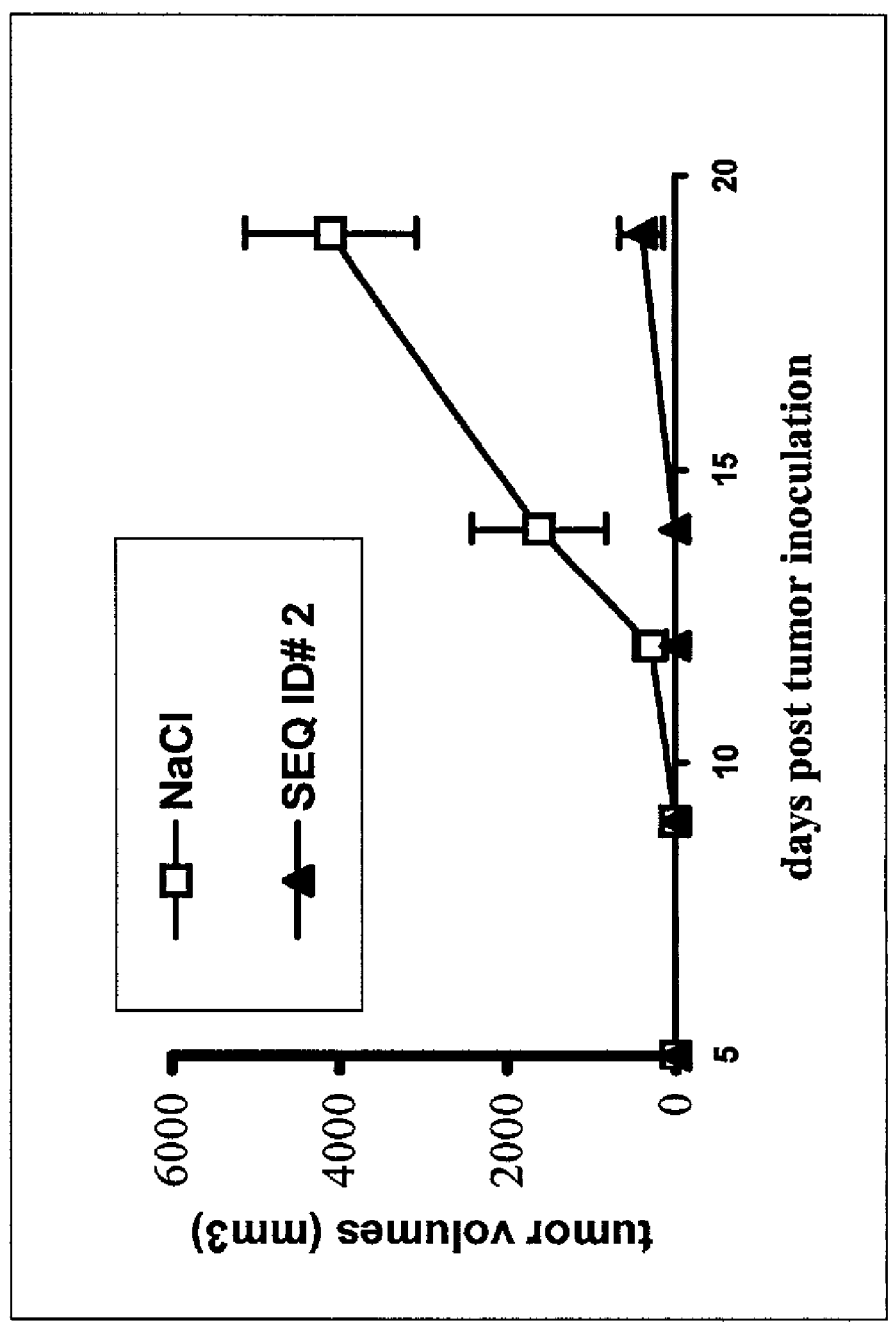
FIG. 12 shows the antitumor effect of an immunostimulating oligonucleotide on a melanoma model.

To determine whether local immunostimulation by an immunostimulating oligonucleotide was also efficient in non-neural cancer, the anti-tumor efficacy of SEQ ID NO: 2was tested in the syngenic B16 melanoma cells/C57B16 mice. C57B16 mice were injected sub cutaneously into the right flank with 100 000 B16 melanoma cells. Referring to FIG. 12, on day 2, 5 and 9 after tumor inoculation, mice were injected at the tumor site either with 50 µl saline or 50 µg of oligonucleotide SEQ ID NO: 2 dissolved in 50 µl saline. Tumor growth was assessed with a caliper, using the formula: Vol.=length×width×width×π)/6.

While all animals injected with saline developed fast growing tumors, treatment with oligonucleotide SEQ ID NO: 2 resulted in a dramatic inhibition of tumor growth when compared to controls injected with saline (p<0.001).

EXAMPLE 15

Antitumor Efficacy of Various Oligonucleotides in the 9L Glioma Model

To determine the optimal sequences for tumor rejection, various oligonucleotides were compared in the sub-cutaneous 9L glioma model. Fisher rats (6 week old) were inoculated into the right flank with 100 000 viable 9L glioma cells. 2 days later, 50 µg oligonucleotides dissolved in 50µl saline were injected at the tumor site. Tumor growth was monitored for at least 3 months, and animals were sacrificed when the tumors reached 3 cm in diameter.

Table 1 shows the percentage of animals that completely rejected the tumor graft on a long-term period of observation. All animals injected with saline developed tumors and were sacrificed within 5 weeks. Despite an increased median survival time, all animals but one treated with the previously disclosed oligonucleotides SEQ ID NO: 2 in WO 98/55495, and SEQ. MYC SEQ ID NO: 56 "5'-AACGTTGAGGGGCAT in Cancer Res. 58, 283–289, 1998 or with the SEQ ID NO: 10 SEQ. 10 which contains only one 5'pur-pur-CG-pyr-pyr-AT motifs had to be sacrificed within 10 weeks. Only oligonucleotides containing three "pur-pur-CG-pyr-pyr-(AT/AA/CT/TT)" motifs gave a significant percentage of long term surviving animals.

TABLE 1

Anti-tumor efficacy of various oligonucleotides in the 9L glioma model.

| | Number of motifs: pur-pur-CG-pyr-pyr | Number of rats | % long term survival | P |
|---|---|---|---|---|
| NaCl | 0 | 22 | 0% | |
| SEQ ID NO:2 | 1 | 15 | 0% | |
| SEQ ID NO:56 | 1 | 12 | 8% | |
| SEQ ID NO:10 | 1 | 6 | 0% | |
| SEQ ID NO:33 | 3 | 12 | 33% | |

TABLE 1-continued

Anti-tumor efficacy of various oligonucleotides in the 9L glioma model.

| | Number of motifs: pur-pur-CG-pyr-pyr | Number of rats | % long term survival | P |
|---|---|---|---|---|
| SEQ ID NO:34 | 3 | 9 | 22% | |
| SEQ ID NO:38 | 3 | 12 | 8% | |
| SEQ ID NO:43 | 3 | 12 | 33% | |
| SEQ ID NO:46 | 3 | 12 | 25% | |

EXAMPLE 16

Oligonucleotide Stimulation of Human B-cells

To study the efficacy of oligonucleotides on the human immune system and to determine the optimal sequence for inmiunostimulation, the mitogenic potency of several oligonucleotides were tested on human B-cells in vitro, purified from surgically resected tonsils. Briefly, tonsils were cut into pieces, and suspended cells were centrifuged on a ficoll gradient. The band corresponding to the lymphocytes was then resuspended in RPMI containing 20% FBS. The suspension was incubated with sheep blood cells activated with AET(2-aminoethyl isothiouronium bromide), then centrifuged on another ficoll gradient to get rid of T-cells. Cell number and viability was checked before each assay. B cells (100 000/wells) were dispensed in triplicate into 96 well microtiter plates in 100 µl RPMI supplemented with 10% FBS. 2 µg/ml oligonucleotide were added for 72 hours, and cells were pulsed with 50 µCi/ml of tritiated thymidine for 18 hours, then harvested and counted. A negative control (medium alone) and a positive control with anti-CD40 ligand protein (Pharmingen, San Diego, Calif.) were included in each assay.

1) Table 2 summarizes 2 different experiments assessing the proliferation induced by oligonucleotides containing from 1 to 3 "pur-pur-CG-pyr-pyr-AT/AA/CT/TT" motifs.

SEQ ID NO: 43: TA AACGTTCT AACGTTCT GACGTCCT was compared to its corresponding oligonucleotides wherein the first motif, or the first two motifs, respectively, were mutated:

SEQ ID NO: 57: TA AAGGTTCT AACGTTCT GACGTCCT

SEQ ID NO: 58: TA AAGGTTCT AACCTTCT GACGTCCT

Similarly, sequences where the first, or first two motifs were mutated were compared:

SEQ ID NO: 35 GACGTCAT AACGTTAT AACGTTAT

SEQ ID NO: 59 TA GAGGTCAT AACGTTAT AACGTTAT

SEQ ID NO: 60 TA GAGGTCAT AACCTTAT AACGTTAT

SEQ. 2 refers to an oligonucleotide previously disclosed in WO 98/55495.

Data shows that oligonucleotides containing 3 motifs are more mitogemc than those containing 2 motifs, which are slightly more mitogenic than those containing 1 motif. In addition, SEQ ID NO: 35 and SEQ ID NO:43 are more immunostimulant than the previously disclosed SEQ ID NO:2 of WO 98/55495.

TABLE 2

| ASSAY 1 | | ASSAY 2 | |
|---|---|---|---|
| | Thymidine uptake mean +/− SD | | Thymidine uptake Mean +/− SD |
| Ctrl | 48 +/− 15 | Ctrl | 51 +/− 8 |
| SEQ ID NO:43 | 4241 +/− 665 | SEQ ID NO:35 | 3410 +/− 932 |
| SEQ ID NO:43' | 1560 +/− 315 | SEQ ID NO:35' | 1810 +/− 120 |
| SEQ ID NO:43" | 1182 +/− 225 | SEQ ID NO:35" | 1509 +/− 272 |
| SEQ ID NO:2 | 3228 +/− 655 | SEQ ID NO:2 | 2446 +/− 308 |

2) Table 3 summarizes 2 experiments assessing the proliferation induced by various oligonucleotides containing 3 "pur-pur-CG-pyr-pyr-(AT/AA/CT/TT)" motifs (SEQ ID NOS: 51–54) and by 3 oligonucleotides containing a "pur-pur-CG-pyr-pyr" motifs previously described in the literature for their immunostimulating or anti-tumoral activity (SEQ ID NO: 2in WO 98/55495, SEQ ID NO: 55 SEQ. K "5'-TCGTCGTTTTGTCGTTTTGTCGTT" in U.S. Pat. No. 6,239,116; and SEQ ID NO: 56 SEQ. MYC "5'-AACGT-TGAGGGGCAT in Cancer Res. 58, 283–289, 1998. Both experiments were repeated at least twice and gave similar results.

All oligonucleotides SEQ. 31 to 46 appeared strongly mitogenic on human B-cells, and this efficacy was greater than the previously disclosed SEQ ID NO: 55 SEQ. K, SEQ ID NO: 2 (WO 98/55495); and SEQ ID NO: 56 SEQ. MYC.

In addition, minor sequence modifications resulted in various activitiesy of the oligonucleotides. For example, oligonucleotides wherein the 3 "pur-pur-CG-pyr-pyr-(AT/AA/CT/TT)" motifs are not the same, appeared more potent than those with 3 identical motifs. (compared SEQ ID NO: 33, 34, 35, 43 to SEQ. 31, 32, 41 and 42). Also, SEQ ID NO: 38 containing AA next to the pur-pur-CG-pyr-pyr motif was less efficient than its corresponding oligonucleotides with AT (SEQ ID NO: 34 or SEQ ID NO: 35), TT (SEQ. 46) or CT (SEQ ID NO: 43) next to the pur-pur-CG-pyr-pyr motif.

TABLE 3 proliferation induced by various oligonucleotides

| ASSAY 1 | | ASSAY 2 | |
|---|---|---|---|
| | Thymidine uptake mean +/− SD | | Thymidine uptake Mean +/− SD |
| CTRL | 39 +/− 13 | Ctrl | 69 +/− 16 |
| SEQ ID NO:31 | 1561 +/− 258 | SEQ ID NO:34 | 1316 +/− 422 |
| SEQ ID NO:32 | 1320 +/− 330 | SEQ ID NO:35 | 1494 +/− 597 |
| SEQ ID NO:33 | 1701 +/− 148 | SEQ ID NO:38 | 1035 +/− 355 |
| SEQ ID NO:34 | 2303 +/− 349 | SEQ ID NO:43 | 1709 +/− 173 |
| SEQ ID NO:35 | 1877 +/− 747 | SEQ ID NO:46 | 1967 +/− 238 |
| SEQ ID NO:41 | 1303 +/− 82 | SEQ ID NO:2 | 1191 +/− 358 |
| SEQ ID NO:42 | 1251 +/− 249 | SEQ ID NO:55 | 1155 +/− 324 |
| SEQ ID NO:43 | 2419 +/− 226 | SEQ ID NO:56 | 137 +/− 60 |

EXAMPLE 17

Combination of Immunostimulating Oligonucleotides and Chemotherapy.

Figure 13:
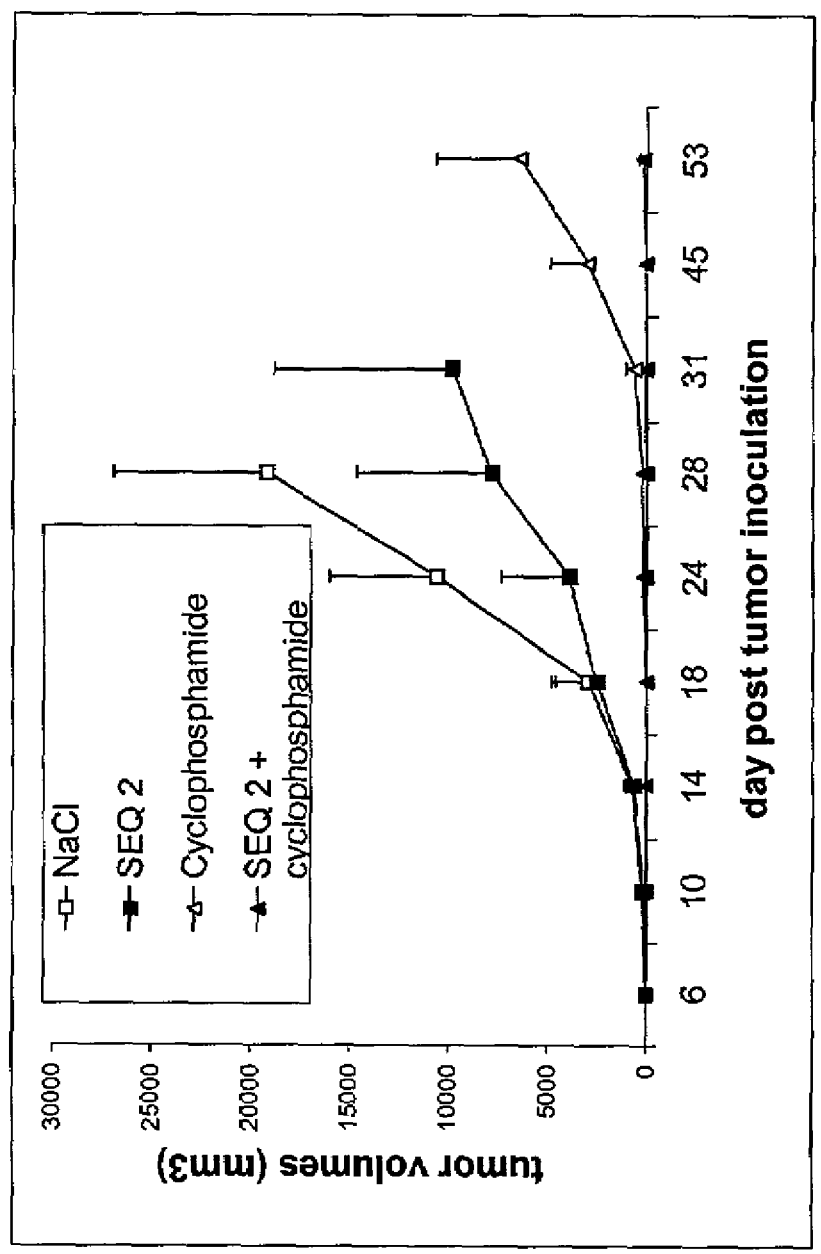
FIG. 13 shows the effect on tumor volume of an injection of a combination of immunostimulating oligonucleotide and cyclophosphamide in the 9L glioma model.

The combination of immunostimulating oligonucleotides and conventional treatments such as radiotherapy or chemotherapy were analyzed for a synergistic effect in the reduction of tumor volumes. Referring to FIG. 13, in the first experiment, Fisher rats were inoculated subcutaneously with 100,000 9L glioma cells, injected I.P. with either saline or 50mg/kg cyclophosphamide on day 3, then injected at the tumor site with either saline or 50 μg oligonucleotide SEQ ID NO 2 on day 5. Tumor growth was assessed with a caliper, using the formula: Vol.(length×width×width×π)/6. Both oligonucleotide and cyclophosphamide alone induced an inhibition of tumor growth, but maximal effects were obtained when both treatments were combined, showing that these treatments have additive or synergistic effects.

Figure 14:
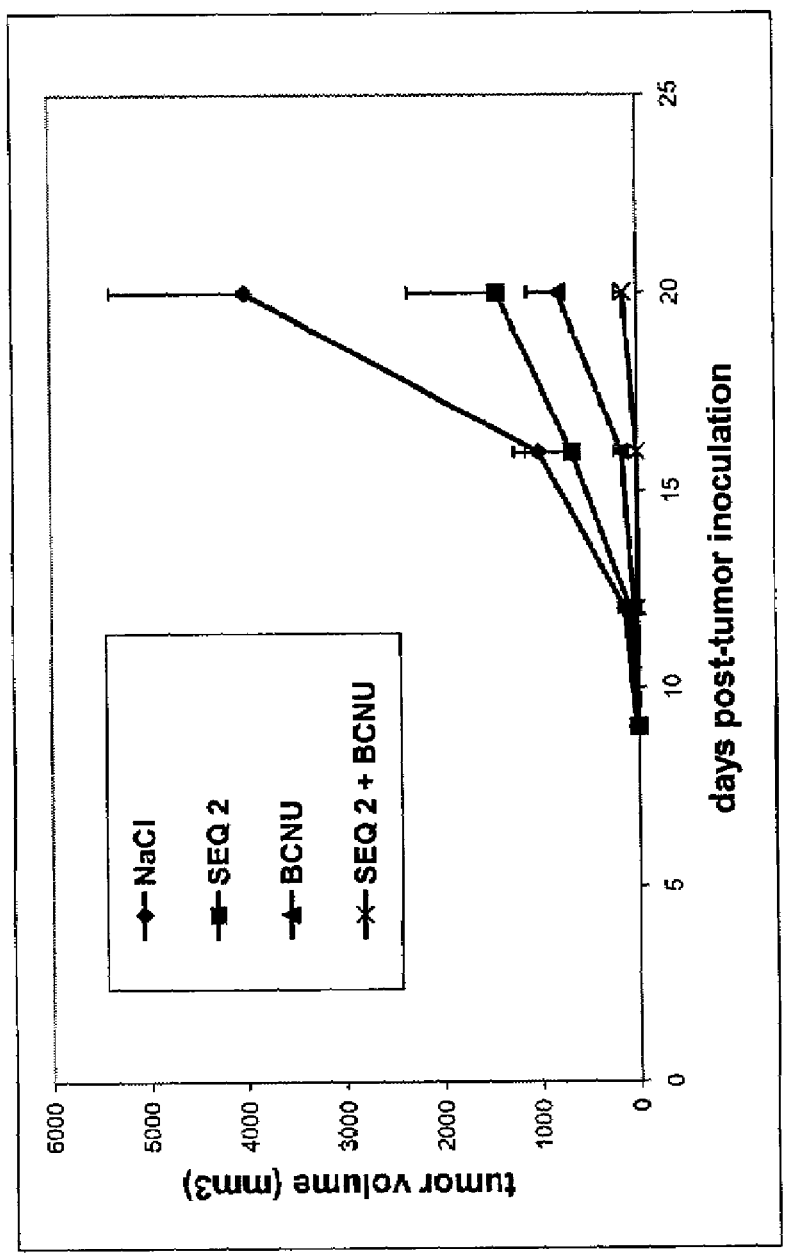
FIG. 14 shows the effect on tumor volume of an injection of a combination of immunostimulating oligonucleotide and BCNU in the RG2 glioma model.

Referring to FIG. 14, in a second experiment, Fisher rats were inoculated sub cutaneously with 100 000 RG2 glioma cells, injected I.P. with either saline or 50mg/kg BCNU on day 2, and injected at the tumor site with either saline or 50 λg oligonucleotide SEQ ID NO 2 on days 2, 5 and 9 post tumor inoculation. Tumor growth was assessed with a caliper, using the formula: Vol.(length×width×width×π)/6. Both oligonucleotide and cyclophosphamide alone induced an inhibition of tumor growth, but maximal effects were obtained when both treatments were combined, showing that these treatments have additive or synergistic effects.

The invention claimed is:

1. A method for treating a solid tumor comprising:
   a) locating a solid tumor in the body of a patient,
   b) surgically removing at least a portion of the solid tumor, and
   c) administering to the patient by direct injection into the remaining tumor or into the tissue surrounding said tumor, or by a combination of direct injection into the remaining tumor or the tissue surrounding said tumor and systemic administration,
   a pharmaceutical composition containing an oligonucleotide comprising at least one octameric motif AACGTTAT (SEQ ID NO: 51),
   wherein the CG in said octameric motif is non-methylated and
   wherein said oligonucleotide is stabilized by a modified backbone comprising a phosphorothioate, a phosphorodithioate, or a phosphodiester-phosphorothioate mixture, or is an oligonucleotide stabilized at a 3' and/or 5' end.

2. The method of claim 1, wherein the oligonucleotide comprises two or three octameric motifs AACGTTAT (SEQ ID NO: 51).

3. The method of claim 1, wherein the oligonucleotide is single-stranded.

4. The method of claim 1, wherein the oligonucleotide length is from 20 to 100 bases or base pairs.

5. The method of claim 1, wherein the oligonucleotide is selected from the group consisting of SEQ ID NO: 9, 10, 16, 21, 31, 33, 34, 35 and 47.

6. The method of claim 1, wherein the oligonucleotide is combined with an encapsulating agent, colloidal dispersion system or a polymer.

7. The method of claim 1, wherein the oligonucleotide is coupled via covalent, ionic or weak bonding, to a compound which is selected from the group consisting of transferrin, folate, antibodies directed against tenascine, EGF receptor, transferrin receptor and FGF receptor.

8. The method of claim 1, wherein the solid tumor is located in the central or peripheral nervous system.

9. The method of claim 1, wherein the solid tumor is selected from the group consisting of astrocytomas, glioblastomas, medulloblastomas, neuroblastomas, melanomas and carcinomas.

* * * * *